US009664693B2

(12) United States Patent
Bonkovsky et al.

(10) Patent No.: US 9,664,693 B2
(45) Date of Patent: May 30, 2017

(54) BIOMARKERS FOR THE IDENTIFICATION OF LIVER DAMAGE

(71) Applicant: The Charlotte-Mecklenburg Hospital Authority, Charlotte, NC (US)

(72) Inventors: Herbert L. Bonkovsky, Charlotte, NC (US); David Foureau, Charlotte, NC (US); H. James Norton, Charlotte, NC (US); Nury Steuerwald, Charlotte, NC (US)

(73) Assignee: THE CHARLOTTE-MECKLENBURG HOSPITAL AUTHORITY, Charlotte, NC (US)

( * ) Notice: Subject to any disclaimer, the term of this patent is extended or adjusted under 35 U.S.C. 154(b) by 0 days.

(21) Appl. No.: 14/438,273

(22) PCT Filed: Oct. 24, 2013

(86) PCT No.: PCT/US2013/066674
§ 371 (c)(1),
(2) Date: Apr. 24, 2015

(87) PCT Pub. No.: WO2014/066676
PCT Pub. Date: May 1, 2014

(65) Prior Publication Data
US 2015/0301066 A1    Oct. 22, 2015

Related U.S. Application Data

(60) Provisional application No. 61/717,977, filed on Oct. 24, 2012.

(51) Int. Cl.
*G01N 33/68* (2006.01)

(52) U.S. Cl.
CPC ..... *G01N 33/6893* (2013.01); *G01N 2333/49* (2013.01); *G01N 2333/503* (2013.01); *G01N 2333/523* (2013.01); *G01N 2333/525* (2013.01); *G01N 2333/54* (2013.01); *G01N 2333/5406* (2013.01); *G01N 2333/5409* (2013.01); *G01N 2333/5412* (2013.01); *G01N 2333/5425* (2013.01); *G01N 2333/5434* (2013.01); *G01N 2333/5437* (2013.01); *G01N 2333/765* (2013.01); *G01N 2800/08* (2013.01); *G01N 2800/085* (2013.01); *G01N 2800/52* (2013.01); *G01N 2800/60* (2013.01)

(58) Field of Classification Search
None
See application file for complete search history.

(56) References Cited

U.S. PATENT DOCUMENTS

2008/0161203 A1* 7/2008 Su .................. C40B 40/10
506/18

OTHER PUBLICATIONS

Takayama H. et al. Serum Levels of Platelet Derived Growth Factor BB and Vascular Endothelial Growth Factor as Prognostic Factors for Patients with Fulminant Hepatic Failure. J of Gastroenterology and Hepatology 26:116-121, 2011.*
Njoku D. Suppressive and Pro-Inflammatory Roles for IL-4 in the Pathogenesis of Experimental Drug Induced Liver Injury. Expert Opinion Drug Metabolism and Toxicology 6(5)519-531, May 2010.*
Tawadrous G. et al. RANTES, TNF alpha, Oxidative Stress, and Hematological Abnormalities in Hepatitis C Virus Infection. J of Investigative Medicine 60(6)878-882, Aug 2012.*
International Search Report and Written Opinion from International Application No. PCT/US2013/066674 dated Mar. 12, 2014.
El-Mowafy A M et al.; "Eicosapentaenoic Acid Ablates Valproate-Induced Liver Oxidative Stress and Cellular Derangement Without Altering its Clearance Rate: Dynamic Synergy and Therapeutic Utility"; *Biochimica and Biophysica Acta. Molecular and Cell Biology of Lipids*; Elsevier, Amsterdam, NL; vol. 1811, No. 7; Apr. 27, 2011; pp. 460-467; XP028378738.
Gang Tan et al.; "Hydrogen Sulfide Attenuates Carbon Tetrachloride-Induced Hepatotoxicity, Liver Cirrhosis and Portal Hypertension in Rats"; *PLOS One*; vol. 6, No. 10; Oct. 14, 2011; p. e25943; XP055095411.
Tse-Min Chen et al.; "Single Dose Intravenous Thioacetamide Administration as a Model of Acute Liver Damage in Rats"; *International Journal of Experimental Pathology*; vol. 89, No. 4; Aug. 17, 2008; pp. 223-231; XP055095565.
Nury Steuerwald et al.; "Chemokine/Cytokine Profiles in Patients with Acute Dili; Results from the US Drug Induced Liver Injury Network"; Hepatology; *The 62nd Annual Meeting of the American Association for the Study of Liver Diseases; The Liver Meeting 2011*; Wiley, USA; San Francisco, CA, USA; vol. 54, No. Suppl. 1; Oct. 1, 2011; p. 529A; XP008166572.
Hugh G Laverty et al.; "The Potential of Cytokines as Safety Biomarkers for Drug-Induced Liver Injury"; *European Journal of Clinical Pharmacology*; Springer, Berlin, DE; vol. 66, No. 10; Aug. 6, 2010; pp. 961-976; XP019840409.
Nury M. Steurwald et al.; "Profiles of Serum Cytokines in Acute Drug-Induced Liver Injury and Their Prognostic Significance"; *PLOS One*; vol. 8, No. 12; Dec. 27, 2013; XP055095423.

* cited by examiner

*Primary Examiner* — Ralph Gitomer
(74) *Attorney, Agent, or Firm* — John P. Zimmer; J. Clinton Wimbish; Smith Moore Leatherwood LLP

(57) ABSTRACT

Methods and kits for characterizing liver damage in an individual are provided. The methods employ the use of immune analytes as biomarkers for detecting liver damage and predicting the likelihood that an individual suffering from liver damage will experience life-threatening liver failure. Concentration values for serum albumin and other identified immune analytes are obtained or determined from a blood sample taken from the individual. The obtained concentration values are then compared to corresponding concentrations from individuals having a healthy liver. By comparing the concentrations, an individual's likelihood of developing life-threatening liver failure and needing a liver transplant within a given time period (e.g., 6 months) can be identified.

13 Claims, 12 Drawing Sheets

| Healthy donors | Innate Inflammation | | | Cellular inflammation | | | | | Humoral inflammation | | | | Resolution of Inflammation | |
|---|---|---|---|---|---|---|---|---|---|---|---|---|---|---|
| | IL-1b | IL-6 | TNFa | IL-12p70 | IFNg | IL-2 | IL-15 | IL-17 | IL-4 | IL-5 | IL-13 | IL-9 | IL-10 | IL-1ra |
| Average | 1.29 | 7.31 | 29.42 | 30.72 | 65.29 | 8.53 | 7.90 | 57.50 | 9.21 | 5.40 | 7.43 | 24.17 | 15.63 | 147.27 |
| STDEV | 0.08 | 7.38 | 24.28 | 51.24 | 58.47 | 23.64 | 15.50 | 22.43 | 2.66 | 5.23 | 15.35 | 15.57 | 52.20 | 51.08 |

"Mixed-immune"

| N=4 | Innate Inflammation | | | Cellular inflammation | | | | | Humoral inflammation | | | | Resolution of Inflammation | |
|---|---|---|---|---|---|---|---|---|---|---|---|---|---|---|
| | IL-1b | IL-6 | TNFa | IL-12p70 | IFNg | IL-2 | IL-15 | IL-17 | IL-4 | IL-5 | IL-13 | IL-9 | IL-10 | IL-1ra |
| DP096192 | 3.97 | 253.40 | 101.73 | 2185.59 | 216.69 | 10.25 | 0.00 | 17.55 | 12.68 | 68.37 | 130.11 | 16.68 | 1008.44 | 203.61 |
| DP050017 | 0.73 | 603.20 | 299.74 | 324.94 | 87.94 | 660.49 | 2.91 | 90.45 | 5.72 | 2.81 | 10.90 | 43.18 | 17.36 | 150.45 |
| DP009424 | 11.32 | 26.63 | 175.34 | 38.74 | 77.25 | 6.13 | 2.77 | 98.33 | 4.13 | 12.86 | 41.67 | 12.87 | 47.36 | 82.74 |
| DP030863 | 0.45 | 17.05 | 34.35 | 136.84 | 37.79 | 23.06 | 8.06 | 46.05 | 4.86 | 19.98 | 20.40 | 8.48 | 44.04 | 72.80 |

*FIG. 5*

"Innate Immune"
N=19

| | Innate Inflammation | | | Cellular inflammation | | | | | Humoral inflammation | | | | Resolution of Inflammation | |
|---|---|---|---|---|---|---|---|---|---|---|---|---|---|---|
| | IL-1b | IL-6 | TNFa | L-12p70 | IFNg | IL-2 | IL-15 | IL-17 | IL-4 | IL-5 | IL-13 | IL-9 | IL-10 | IL-1ra |
| DP026116 | 2.20 | 17.23 | 71.66 | 20.33 | 80.41 | 13.68 | 17.18 | 77.48 | 8.31 | 3.53 | 2.82 | 13.20 | 7.43 | 248.39 |
| DP052264 | 2.75 | 970.49 | 0.00 | 15.66 | 51.58 | 2.39 | 15.15 | 7.93 | 1.25 | 0.77 | 1.75 | 13.07 | 2493.46 | 328.67 |
| DP059111 | 2.41 | 19.35 | 51.91 | 54.77 | 96.01 | 20.95 | 15.02 | 52.94 | 7.11 | 6.46 | 9.64 | 36.90 | 9.58 | 302.35 |
| DP148185 | 2.38 | 31.74 | 30.88 | 27.37 | 80.01 | 1.78 | 0.00 | 24.47 | 5.71 | 4.91 | 4.01 | 17.11 | 2.41 | 719.63 |
| DP040922 | 2.46 | 46.21 | 19.54 | 21.51 | 60.12 | 3.76 | 3.87 | 31.60 | 4.62 | 2.55 | 3.04 | 16.03 | 8.66 | 425.29 |
| DP010496 | 2.95 | 17.95 | 36.08 | 5.92 | 18.38 | 0.00 | 0.00 | 12.17 | 3.63 | 0.82 | 1.11 | 8.63 | 0.00 | 62.80 |
| DP037819 | 3.17 | 20.97 | 41.90 | 36.22 | 47.01 | 14.46 | 8.91 | 49.74 | 4.73 | 7.15 | 7.66 | 17.65 | 33.18 | 441.51 |
| DP039103 | 2.79 | 22.00 | 41.32 | 32.08 | 71.76 | 9.54 | 1.53 | 47.35 | 6.07 | 3.82 | 5.35 | 15.57 | 16.95 | 275.33 |
| DP053334 | 48.24 | 469.16 | 31.97 | 11.92 | 75.78 | 4.82 | 4.31 | 55.04 | 6.21 | 3.96 | 2.38 | 20.50 | 15.35 | 142.51 |
| DP077592 | 0.99 | 19.35 | 70.84 | 17.21 | 42.78 | 13.88 | 2.76 | 38.67 | 5.28 | 4.04 | 2.06 | 15.51 | 9.78 | 168.55 |
| DP016165 | 0.00 | 17.23 | 3.02 | 7.56 | 18.09 | 0.00 | 0.00 | 40.04 | 5.38 | 0.71 | 0.45 | 12.98 | 4.69 | 259.25 |
| DP036428 | 0.00 | 117.34 | 0.00 | 1.38 | 0.00 | 0.00 | 0.33 | 0.00 | 0.00 | 0.74 | 0.70 | 0.00 | 1.69 | 701.44 |
| DP016272 | 0.44 | 385.49 | 1.33 | 3.47 | 15.86 | 0.00 | 0.00 | 3.13 | 3.30 | 0.53 | 0.60 | 0.60 | 0.26 | 89.56 |
| DP006214 | 0.26 | 20.52 | 12.61 | 22.04 | 50.71 | 0.00 | 0.00 | 32.01 | 10.26 | 2.16 | 1.43 | 12.98 | 1.97 | 89.56 |
| DP012313 | 1.45 | 21.90 | 25.67 | 21.64 | 73.14 | 6.72 | 7.60 | 53.28 | 11.56 | 7.26 | 2.84 | 17.77 | 10.96 | 169.92 |
| DP095832 | 0.69 | 310.38 | 10.36 | 5.34 | 24.42 | 0.00 | 0.00 | 0.00 | 4.86 | 3.38 | 1.50 | 2.63 | 2.57 | 90.42 |
| DP079993 | 0.93 | 16.32 | 15.92 | 19.76 | 39.73 | 2.15 | 0.00 | 26.09 | 4.63 | 2.68 | 1.51 | 10.02 | 0.83 | 150.33 |
| DP098832 | 2.05 | 590.37 | 17.59 | 15.34 | 70.79 | 0.00 | 0.00 | 18.39 | 5.42 | 2.99 | 1.94 | 11.02 | 12.66 | 1406.11 |
| DP059540 | 1.26 | 16.42 | 16.07 | 19.58 | 50.13 | 3.99 | 3.72 | 44.31 | 6.45 | 3.37 | 2.94 | 17.48 | 5.34 | 96.87 |

*FIG. 5*
(Continued)

| "Adaptive Immune" N=21 | Innate Inflammation | | | | Cellular inflammation | | | | Humoral inflammation | | | | Resolution of Inflammation | | |
|---|---|---|---|---|---|---|---|---|---|---|---|---|---|---|---|
| | IL-1b | IL-6 | TNFa | IL-12p70 | IFNg | IL-2 | IL-15 | IL-17 | IL-4 | IL-5 | IL-13 | IL-9 | IL-10 | IL-1ra | |
| DP009746 | 12.01 | 79.44 | 326.50 | 2.81 | 152.60 | 11.40 | 2.94 | 56.55 | 5.00 | 1.25 | 1.29 | 11.90 | 0.00 | 120.57 | TH1 type N=3 |
| DP059218 | 3.27 | 18.76 | 56.66 | 30.66 | 285.09 | 11.28 | 6.59 | 44.25 | 7.37 | 5.86 | 4.77 | 23.60 | 6.49 | 312.72 | |
| DP024939 | 2.53 | 14.03 | 70.17 | 37.13 | 0.00 | 16.67 | 28.87 | 34.43 | 0.47 | 3.44 | 8.73 | 0.11 | 14.80 | 4.73 | |
| DP038996 | 3.22 | 18.02 | 120.91 | 35.93 | 91.00 | 12.32 | 11.34 | 122.26 | 11.27 | 9.64 | 13.47 | 33.35 | 11.05 | 240.93 | TH17 type N=12 |
| DP006535 | 2.20 | 33.88 | 31.71 | 47.34 | 51.78 | 5.08 | 3.77 | 94.57 | 8.75 | 7.49 | 5.50 | 33.28 | 5.12 | 244.78 | |
| DP007606 | 1.82 | 11.64 | 33.11 | 15.47 | 25.82 | 3.41 | 0.00 | 80.77 | 3.74 | 9.34 | 3.90 | 12.98 | 9.40 | 176.76 | |
| DP007927 | 0.91 | 14.30 | 20.69 | 14.74 | 30.20 | 6.13 | 0.00 | 99.13 | 4.86 | 3.08 | 1.20 | 17.29 | 4.26 | 105.01 | |
| DP051515 | 1.72 | 10.97 | 44.54 | 44.79 | 38.32 | 25.27 | 13.26 | 114.68 | 5.83 | 5.03 | 19.33 | 9.65 | 3.65 | 235.60 | |
| DP010600 | 0.61 | 5.79 | 23.42 | 8.61 | 30.74 | 5.08 | 6.79 | 156.71 | 5.77 | 2.25 | 1.66 | 14.29 | 2.83 | 69.20 | |
| DP013276 | 2.07 | 11.56 | 34.73 | 58.44 | 20.31 | 15.39 | 15.72 | 139.08 | 3.94 | 7.13 | 2.82 | 7.60 | 13.83 | 86.15 | |
| DP077352 | 1.50 | 8.82 | 36.57 | 35.04 | 47.94 | 7.33 | 8.00 | 93.06 | 6.47 | 5.62 | 4.28 | 20.91 | 4.91 | 124.94 | |
| DP042205 | 0.37 | 5.18 | 15.51 | 6.18 | 53.52 | 2.03 | 5.54 | 98.91 | 6.32 | 1.72 | 6.29 | 37.77 | 3.45 | 132.77 | |
| DP039316 | 1.09 | 4.98 | 4.39 | 12.83 | 51.58 | 3.45 | 18.22 | 86.16 | 7.94 | 1.70 | 2.70 | 17.01 | 11.95 | 89.24 | |
| DP008033 | 0.83 | 4.40 | 11.73 | 12.18 | 56.59 | 0.00 | 0.00 | 91.10 | 8.36 | 1.80 | 2.92 | 17.63 | 2.26 | 132.76 | |
| DP009531 | 1.55 | 7.56 | 37.78 | 54.23 | 75.14 | 5.26 | 0.00 | 89.11 | 7.16 | 7.31 | 7.35 | 37.21 | 1.97 | 185.64 | |
| DP038140 | 3.42 | 28.17 | 116.57 | 35.93 | 45.73 | 14.12 | 12.38 | 40.83 | 5.56 | 13.34 | 7.57 | 24.39 | 18.78 | 188.41 | TH2 Type |
| DP038354 | 2.20 | 16.25 | 38.98 | 31.96 | 65.94 | 23.62 | 9.97 | 50.39 | 6.60 | 4.41 | 3.58 | 44.43 | 5.63 | 243.59 | TH9 Type N=5 |
| DP017770 | 0.14 | 33.68 | 8.20 | 10.92 | 37.80 | 5.26 | 0.00 | 42.75 | 7.61 | 0.53 | 1.48 | 2194.20 | 0.00 | 79.34 | |
| DP005144 | 0.68 | 20.59 | 23.61 | 14.90 | 48.67 | 4.54 | 21.97 | 47.44 | 7.53 | 2.96 | 1.75 | 115.87 | 13.30 | 136.09 | |
| DP004716 | 0.13 | 6.70 | 3.37 | 17.25 | 28.73 | 0.00 | 7.56 | 28.05 | 3.82 | 1.28 | 1.97 | 316.98 | 1.33 | 95.71 | |
| DP037177 | 1.28 | 9.08 | 46.60 | 22.00 | 50.13 | 7.63 | 1.71 | 23.96 | 5.19 | 7.63 | 3.27 | 113.64 | 4.20 | 139.29 | |

FIG. 5
(Continued)

"Normal immune"
N=8

| | Innate Inflammation | | | Cellular inflammation | | | | | Humoral inflammation | | | | Resolution of Inflammation | |
|---|---|---|---|---|---|---|---|---|---|---|---|---|---|---|
| | IL-1b | IL-6 | TNFa | IL-12p70 | IFNg | IL-2 | IL-15 | IL-17 | IL-4 | IL-5 | IL-13 | IL-9 | IL-10 | IL-1ra |
| DP054617 | 0.79 | 9.70 | 7.32 | 9.59 | 38.32 | 0.80 | 2.50 | 62.49 | 8.67 | 2.34 | 3.24 | 9.65 | 3.18 | 115.11 |
| DP037605 | 1.35 | 8.90 | 46.60 | 28.49 | 67.35 | 6.97 | 0.00 | 55.77 | 11.20 | 3.79 | 2.26 | 23.36 | 5.49 | 144.12 |
| DP038461 | 1.04 | 7.34 | 10.31 | 10.12 | 47.20 | 3.99 | 0.00 | 46.73 | 8.54 | 3.12 | 2.70 | 20.25 | 8.11 | 247.82 |
| DP011671 | 1.40 | 9.62 | 32.61 | 29.25 | 82.43 | 2.69 | 3.87 | 28.77 | 6.94 | 3.73 | 4.21 | 17.27 | 12.90 | 179.18 |
| DP035893 | 0.53 | 3.02 | 8.96 | 9.50 | 34.07 | 0.00 | 2.16 | 40.00 | 9.74 | 1.64 | 2.34 | 4.15 | 2.22 | 143.37 |
| DP047128 | 0.80 | 3.45 | 16.09 | 16.29 | 41.48 | 1.07 | 4.91 | 39.61 | 10.61 | 2.99 | 2.77 | 2.80 | 4.27 | 159.29 |
| DP040279 | 1.07 | 11.03 | 26.59 | 19.09 | 42.01 | 2.30 | 4.80 | 79.89 | 4.58 | 5.24 | 3.87 | 10.23 | 14.93 | 118.64 |
| DP022562 | 1.33 | 5.73 | 36.57 | 18.39 | 64.51 | 7.40 | 10.71 | 51.94 | 6.76 | 5.96 | 12.57 | 34.46 | 8.38 | 201.81 |

*FIG. 5*
(Continued)

| | Innate Inflammation | | | Cellular inflammation | | | | | Humoral inflammation | | | | Resolution of Inflammation | |
|---|---|---|---|---|---|---|---|---|---|---|---|---|---|---|
| Healthy donors | IL-1b | IL-6 | TNFa | IL-12p70 | IFNg | IL-2 | IL-15 | IL-17 | IL-4 | IL-5 | IL-13 | IL-9 | IL-10 | IL-1ra |
| Average | 1.29 | 7.31 | 29.42 | 30.72 | 65.29 | 8.53 | 7.90 | 57.50 | 9.21 | 5.40 | 7.43 | 24.17 | 15.63 | 147.27 |
| SD | 0.08 | 7.38 | 24.28 | 51.24 | 58.47 | 23.64 | 15.50 | 22.43 | 2.66 | 5.23 | 15.35 | 15.57 | 52.20 | 51.08 |

"Mixed-immune" at DILI onset

| | Innate Inflammation | | | Cellular inflammation | | | | | Humoral inflammation | | | | Resolution of Inflammation | |
|---|---|---|---|---|---|---|---|---|---|---|---|---|---|---|
| | IL-1b | IL-6 | TNFa | IL-12p70 | IFNg | IL-2 | IL-15 | IL-17 | IL-4 | IL-5 | IL-13 | IL-9 | IL-10 | IL-1ra |
| DP096222 | 13.34 | 47.36 | 298.47 | 636.27 | 626.47 | 0.00 | 0.00 | 0.00 | 8.51 | 69.12 | 95.73 | 10.94 | 373.32 | 663.29 |
| DP009452 | 18.83 | 24.81 | 143.58 | 56.36 | 82.85 | 6.72 | 5.54 | 67.49 | 5.12 | 15.76 | 28.23 | 6.37 | 22.64 | 76.32 |

"Innate Immune" at DILI onset

| | Innate Inflammation | | | Cellular inflammation | | | | | Humoral inflammation | | | | Resolution of Inflamm | |
|---|---|---|---|---|---|---|---|---|---|---|---|---|---|---|
| | IL-1b | IL-6 | TNFa | IL-12p70 | IFNg | IL-2 | IL-15 | IL-17 | IL-4 | IL-5 | IL-13 | IL-9 | IL-10 | IL-1ra |
| DP026142 | 1.43 | 9.25 | 56.53 | 10.47 | 96.47 | 4.89 | 1.71 | 57.55 | 9.34 | 2.29 | 1.68 | 18.86 | 3.26 | 287.89 |
| DP040948 | 0.21 | 1.99 | 2.38 | 6.09 | 26.58 | 0.00 | 1.96 | 66.31 | 6.73 | 1.72 | 2.27 | 11.38 | 0.56 | 76.32 |
| DP037845 | 3.48 | 18.11 | 27.34 | 56.73 | 96.47 | 25.38 | 19.73 | 113.00 | 7.03 | 10.48 | 8.74 | 24.48 | 12.31 | 234.07 |
| DP053360 | 0.48 | 30.73 | 16.09 | 12.40 | 11.22 | 93.18 | 1.50 | 76.98 | 1.87 | 1.37 | 1.77 | 0.00 | 1.15 | 51.66 |
| DP077622 | 1.72 | 36.65 | 42.19 | 20.81 | 72.24 | 53.16 | 0.86 | 45.40 | 7.67 | 3.73 | 2.97 | 18.81 | 0.40 | 182.83 |
| DP006240 | 0.00 | 1.82 | 0.00 | 6.52 | 31.83 | 0.00 | 0.00 | 64.36 | 9.15 | 0.53 | 0.52 | 6.79 | 0.00 | 72.57 |
| DP080022 | 5.83 | 20.97 | 101.10 | 117.89 | 183.17 | 0.00 | 0.00 | 73.12 | 6.75 | 13.56 | 11.12 | 12.33 | 21.92 | 399.93 |

FIG. 6

"Adaptive Immune"   at DILI onset

| | Innate Inflammation | | | Cellular inflammation | | | | | Humoral inflammation | | | | Resolution of Inflammation | | |
|---|---|---|---|---|---|---|---|---|---|---|---|---|---|---|---|
| | IL-1b | IL-6 | TNFa | IL-12p70 | IFNg | IL-2 | IL-15 | IL-17 | IL-4 | IL-5 | IL-13 | IL-9 | IL-10 | IL-1ra | |
| DP006561 | 1.45 | 7.65 | 27.55 | 29.19 | 21.42 | 2.26 | 0.00 | 102.77 | 5.36 | 4.91 | 3.90 | 7.60 | 3.54 | 98.12 | TH17 @ onset |
| DP007631 | 2.58 | 7.98 | 32.64 | 18.82 | 25.27 | 3.06 | 0.00 | 137.28 | 4.81 | 10.82 | 5.34 | 8.42 | 3.11 | 127.53 | |
| DP051541 | 0.97 | 4.76 | 14.00 | 13.59 | 26.14 | 0.00 | 0.00 | 51.19 | 4.09 | 2.09 | 2.01 | 12.95 | 0.00 | 103.74 | |
| DP042225 | 0.20 | 1.47 | 5.43 | 7.72 | 54.48 | 3.18 | 2.56 | 109.24 | 8.43 | 1.11 | 1.03 | 19.92 | 2.28 | 113.92 | |
| DP038166 | 2.17 | 10.46 | 60.84 | 33.50 | 48.47 | 6.38 | 6.52 | 53.74 | 7.30 | 4.79 | 6.07 | 17.58 | 2.27 | 181.61 | TH2 @ onset |
| DP017796 | 0.22 | 4.17 | 4.73 | 81.81 | 11.37 | 5.78 | 0.00 | 90.04 | 2.76 | 1.62 | 0.98 | 512.82 | 0.00 | 42.57 | TH9 @ onset |
| DP005170 | 0.92 | 5.70 | 16.09 | 17.25 | 44.11 | 1.89 | 4.44 | 29.63 | 5.10 | 3.25 | 4.14 | 14.75 | 1.20 | 150.45 | |
| DP004742 | 2.11 | 11.11 | 59.23 | 46.23 | 190.16 | 7.92 | 15.20 | 39.25 | 9.15 | 13.59 | 14.79 | 795.68 | 12.77 | 571.85 | |

"Normal Immune"   at DILI onset

| | Innate Inflammation | | | Cellular inflammation | | | | | Humoral inflammation | | | | Resolution of Inflammation | |
|---|---|---|---|---|---|---|---|---|---|---|---|---|---|---|
| | IL-1b | IL-6 | TNFa | IL-12p70 | IFNg | IL-2 | IL-15 | IL-17 | IL-4 | IL-5 | IL-13 | IL-9 | IL-10 | IL-1ra |
| DP054644 | 4.02 | 17.31 | 73.44 | 76.09 | 172.63 | 0.00 | 0.00 | 0.00 | 5.98 | 10.52 | 7.91 | 11.7 | 18.31 | 301.60 |
| DP047154 | 0.23 | 1.05 | 3.38 | 3.47 | 18.38 | 0.00 | 0.00 | 7.20 | 2.85 | 0.77 | 0.61 | 0.00 | 0.00 | 47.00 |
| DP040306 | 2.85 | 9.95 | 45.17 | 105.49 | 105.17 | 0.00 | 0.00 | 0.00 | 3.96 | 7.47 | 9.87 | 8.78 | 61.86 | 237.70 |

*FIG. 6*
(Continued)

Uncategorized at DILI onset

| | Innate Inflammation | | | Cellular inflammation | | | | | Humoral inflammation | | | | Resolution of Inflammation | |
|---|---|---|---|---|---|---|---|---|---|---|---|---|---|---|
| | IL-1b | IL-6 | TNFa | IL-12p70 | IFNg | IL-2 | IL-15 | IL-17 | IL-4 | IL-5 | IL-13 | IL-9 | IL-10 | IL-1ra |
| DP004314 | 0.32 | 2.65 | 15.51 | 9.03 | 26.58 | 0.00 | 2.36 | 42.24 | 10.17 | 2.34 | 1.97 | 7.28 | 0.15 | 125.71 |
| DP042118 | 0.94 | 6.15 | 25.48 | 153.93 | 36.80 | 4.27 | 0.00 | 44.62 | 7.76 | 8.38 | 9.36 | 17.80 | 14.86 | 158.72 |
| DP035492 | 0.91 | 3.04 | 10.19 | 13.13 | 26.14 | 0.00 | 0.00 | 56.73 | 3.35 | 2.32 | 2.53 | 1.68 | 0.00 | 53.26 |
| DP026677 | 0.10 | 0.07 | 0.47 | 4.29 | 20.32 | 0.00 | 0.00 | 16.93 | 4.17 | 0.87 | 0.29 | 4.90 | 0.00 | 53.26 |
| DP079902 | 5.73 | 22.30 | 93.04 | 131.46 | 209.15 | 0.00 | 0.00 | 153.44 | 7.8 | 14.25 | 12.31 | 16.31 | 26.20 | 420.63 |
| DP048652 | 0.91 | 2.24 | 8.14 | 24.15 | 6.68 | 0.00 | 2.88 | 59.20 | 0.98 | 1.81 | 5.58 | 0.00 | 0.18 | 55.18 |
| DP078942 | 1.46 | 4.21 | 21.52 | 22.17 | 58.27 | 0.00 | 0.00 | 0.00 | 2.18 | 4.5 | 3 | 0.75 | 3.24 | 41.07 |
| DP099102 | 2.76 | 11.17 | 52.84 | 63.19 | 126.51 | 0.00 | 0.00 | 52.77 | 3.96 | 9.01 | 7.94 | 10.69 | 20.66 | 212.50 |
| DP054537 | 1.98 | 6.26 | 31.94 | 38.99 | 64.02 | 0.00 | 0.00 | 16.93 | 2.35 | 5.22 | 4.03 | 8.19 | 8.54 | 117.75 |
| DP007845 | 0.00 | 2.65 | 0.00 | 2.81 | 5.65 | 0.00 | 0.00 | 82.75 | 3.08 | 0.17 | 0.00 | 4.64 | 0.00 | 55.80 |
| DP097542 | 1.68 | 7.76 | 26.59 | 25.73 | 58.66 | 6.13 | 4.44 | 43.10 | 6.16 | 3.95 | 3.61 | 16.42 | 0.86 | 169.50 |
| DP147735 | 3.34 | 12.14 | 66.45 | 77.59 | 162.06 | 0.00 | 0.00 | 15.78 | 5.77 | 9.8 | 6.22 | 17.51 | 15.29 | 210.20 |

FIG. 6
(Continued)

| Healthy donors | Innate Inflammation | | | Cellular inflammation | | | | | Humoral inflammation | | | | NFkB-dependent | | IRF-dependent |
|---|---|---|---|---|---|---|---|---|---|---|---|---|---|---|---|
| | IL-1b | IL-6 | TNFa | L-12p70 | IFNg | IL-2 | IL-15 | IL-17 | IL-4 | IL-5 | IL-13 | IL-9 | MIP-1a | MIP-1b | MCP-1 | IP-10 |
| Average | 1.29 | 7.31 | 29.42 | 30.72 | 65.29 | 8.53 | 7.90 | 57.50 | 9.21 | 5.40 | 7.43 | 24.17 | 4.80 | 100.85 | 44.70 | 2015.75 |
| STDEV | 0.08 | 7.38 | 24.28 | 51.24 | 58.47 | 23.64 | 15.50 | 22.43 | 2.66 | 5.23 | 15.35 | 15.57 | 4.70 | 31.82 | 23.59 | 7492.64 |

" Innate Immune "

| | Innate Inflammation | | | Cellular inflammation | | | | | Humoral inflammation | | | | NFkB-dependent | | | IRF-dependent |
|---|---|---|---|---|---|---|---|---|---|---|---|---|---|---|---|---|
| | IL-1b | IL-6 | TNFa | L-12p70 | IFNg | IL-2 | IL-15 | IL-17 | IL-4 | IL-5 | IL-13 | IL-9 | MIP-1a | MIP-1b | MCP-1 | IP-10 |
| DP026116 | 2.20 | 17.23 | 71.66 | 20.33 | 80.41 | 13.68 | 17.18 | 77.48 | 8.31 | 3.53 | 2.82 | 13.20 | 6.37 | 210.44 | 40.60 | 2972.70 |
| DP052264 | 2.75 | 970.49 | 0.00 | 15.66 | 51.58 | 2.39 | 15.15 | 7.93 | 1.25 | 0.77 | 1.75 | 13.07 | 52.31 | 133.10 | 271.66 | 4985.58 |
| DP059111 | 2.41 | 39.35 | 51.91 | 54.77 | 96.01 | 20.95 | 15.02 | 52.94 | 7.11 | 6.46 | 9.64 | 36.90 | 12.01 | 158.40 | 121.92 | 1461.82 |
| DP148185 | 2.38 | 31.74 | 30.88 | 27.37 | 80.01 | 1.78 | 0.00 | 24.47 | 5.71 | 4.91 | 4.01 | 17.11 | 5.97 | 75.27 | 86.00 | 2325.54 |
| DP040922 | 2.46 | 46.21 | 19.54 | 21.51 | 60.12 | 3.76 | 3.87 | 31.60 | 4.62 | 2.55 | 3.04 | 16.03 | 10.50 | 138.70 | 17.67 | 665.65 |
| DP010496 | 2.95 | 17.95 | 36.08 | 5.92 | 18.38 | 0.00 | 0.00 | 12.17 | 3.63 | 0.82 | 1.11 | 8.63 | 32.14 | 336.15 | 17.01 | 3009.72 |
| DP037819 | 3.17 | 20.97 | 41.90 | 36.22 | 47.01 | 14.46 | 8.91 | 49.74 | 4.73 | 7.15 | 7.66 | 17.65 | 28.24 | 191.63 | 31.23 | 12186.73 |
| DP039103 | 2.79 | 22.00 | 41.32 | 32.08 | 71.76 | 9.54 | 1.53 | 47.35 | 6.07 | 3.82 | 5.35 | 15.57 | 17.21 | 206.37 | 22.22 | 15205.33 |
| DP053334 | 48.24 | 469.16 | 31.97 | 11.92 | 75.78 | 4.82 | 4.31 | 55.04 | 6.21 | 3.96 | 2.38 | 20.50 | 80.06 | 473.75 | 399.29 | 8259.86 |
| DP077592 | 0.99 | 19.35 | 70.84 | 17.21 | 42.78 | 13.88 | 2.76 | 38.67 | 5.28 | 4.04 | 2.06 | 15.51 | 6.38 | 317.95 | 23.57 | 5020.98 |
| DP016165 | 0.00 | 17.23 | 3.02 | 7.56 | 18.09 | 0.00 | 0.00 | 40.04 | 5.38 | 0.71 | 0.45 | 12.98 | 3.63 | 135.50 | 20.42 | 718.38 |
| DP036428 | 0.00 | 117.34 | 0.00 | 1.38 | 0.00 | 0.00 | 0.33 | 0.00 | 0.00 | 0.74 | 0.70 | 0.00 | 2.24 | 61.52 | 0.00 | 391.45 |
| DP016272 | 0.44 | 385.49 | 1.33 | 3.47 | 15.86 | 0.00 | 0.00 | 3.13 | 3.30 | 0.53 | 0.60 | 0.60 | 3.30 | 276.74 | 58.18 | 426.17 |
| DP006214 | 0.26 | 20.52 | 12.61 | 22.04 | 50.71 | 6.72 | 7.60 | 32.01 | 10.26 | 2.16 | 1.43 | 12.98 | 4.46 | 106.81 | 17.85 | 2301.01 |
| DP012313 | 1.45 | 21.90 | 25.67 | 21.64 | 73.14 | 0.00 | 0.00 | 53.28 | 11.56 | 7.26 | 2.84 | 17.77 | 2.39 | 135.65 | 93.32 | 48049.82 |
| DP095832 | 0.69 | 310.38 | 10.36 | 5.34 | 24.42 | 2.15 | 0.00 | 0.00 | 4.86 | 3.38 | 1.50 | 2.63 | 0.00 | 49.31 | 20.44 | 1634.17 |
| DP079993 | 0.93 | 16.32 | 15.92 | 19.76 | 39.73 | 0.00 | 0.00 | 26.09 | 4.63 | 2.68 | 1.51 | 10.02 | 5.03 | 52.14 | 50.91 | 762.19 |
| DP098832 | 2.05 | 590.37 | 17.59 | 15.34 | 70.79 | 3.99 | 0.00 | 18.39 | 5.42 | 2.99 | 1.94 | 11.02 | 0.00 | 135.29 | 308.89 | 39266.38 |
| DP059540 | 1.26 | 16.42 | 16.07 | 19.58 | 50.13 | 3.99 | 3.72 | 44.31 | 6.45 | 3.37 | 2.94 | 17.48 | 2.04 | 63.92 | 26.96 | 1191.28 |

| | Innate Inflammation | | | Cellular inflammation | | | | | Humoral inflammation | | | | NFkB-dependent | | IRF-dependent |
|---|---|---|---|---|---|---|---|---|---|---|---|---|---|---|---|
| "Adaptive Immune" | IL-1b | IL-6 | TNFa | IL-12p70 | IFNg | IL-2 | IL-15 | IL-17 | IL-4 | IL-5 | IL-13 | IL-9 | MIP-1a | MIP-1b | MCP-1 | IP-10 |
| DP009746 | 12.01 | 79.44 | 326.50 | 2.81 | 152.60 | 11.40 | 2.94 | 56.55 | 5.00 | 1.25 | 1.29 | 11.90 | 0.00 | 49.36 | 64.06 | 1249.28 |
| DP059218 | 3.27 | 18.76 | 56.66 | 30.66 | 285.99 | 11.28 | 6.59 | 44.25 | 7.37 | 5.86 | 4.77 | 23.60 | 8.20 | 168.53 | 111.43 | 2930.74 |
| DP024939 | 2.53 | 14.03 | 70.17 | 37.13 | 0.00 | 16.67 | 28.83 | 34.43 | 0.47 | 3.44 | 8.73 | 0.11 | 0.00 | 24.10 | 8.75 | 71.87 |
| DP038996 | 3.22 | 18.02 | 120.91 | 35.93 | 91.00 | 12.32 | 11.34 | 122.26 | 11.27 | 9.64 | 13.47 | 33.35 | 7.16 | 180.70 | 52.51 | 1624.58 |
| DP006535 | 2.20 | 33.88 | 31.71 | 47.34 | 51.78 | 5.08 | 3.77 | 94.57 | 8.75 | 7.49 | 5.50 | 33.28 | 10.23 | 83.23 | 21.59 | 1019.62 |
| DP007606 | 1.82 | 11.64 | 33.11 | 15.47 | 25.82 | 3.41 | 0.00 | 80.77 | 3.74 | 9.34 | 3.90 | 12.98 | 4.81 | 75.16 | 50.91 | 4273.63 |
| DP007927 | 0.91 | 14.30 | 20.69 | 14.74 | 30.20 | 6.13 | 0.00 | 99.13 | 4.86 | 3.08 | 1.20 | 17.29 | 4.04 | 104.10 | 44.02 | 2398.09 |
| DP051515 | 1.72 | 10.97 | 44.54 | 44.79 | 38.32 | 25.27 | 13.26 | 114.68 | 5.83 | 5.03 | 19.33 | 9.65 | 5.62 | 88.75 | 42.07 | 741.29 |
| DP010600 | 0.61 | 5.79 | 23.42 | 8.61 | 30.74 | 5.08 | 6.79 | 156.71 | 5.77 | 2.25 | 1.66 | 14.29 | 1.55 | 55.76 | 12.69 | 1175.54 |
| DP013276 | 2.07 | 11.56 | 34.73 | 58.44 | 20.31 | 15.39 | 15.72 | 139.08 | 3.94 | 7.13 | 2.82 | 7.60 | 5.26 | 84.88 | 5.59 | 998.19 |
| DP077352 | 1.50 | 8.82 | 36.57 | 35.04 | 47.94 | 7.33 | 8.00 | 93.96 | 6.47 | 5.62 | 4.28 | 20.91 | 5.71 | 65.28 | 37.89 | 226.93 |
| DP042205 | 0.37 | 5.18 | 15.51 | 6.18 | 53.52 | 2.03 | 5.54 | 98.91 | 6.32 | 1.72 | 6.29 | 37.77 | 0.67 | 44.65 | 5.03 | 222.60 |
| DP039316 | 1.09 | 4.98 | 4.39 | 12.83 | 51.58 | 3.45 | 18.22 | 86.16 | 7.94 | 1.70 | 2.70 | 17.01 | 4.22 | 70.45 | 30.02 | 10040.55 |
| DP008033 | 0.83 | 4.40 | 11.73 | 12.18 | 56.59 | 0.00 | 0.00 | 91.10 | 8.36 | 1.80 | 2.92 | 17.63 | 1.24 | 82.72 | 11.22 | 2377.60 |
| DP009531 | 1.55 | 7.56 | 37.78 | 54.23 | 75.14 | 5.26 | 0.00 | 89.11 | 7.16 | 7.31 | 2.92 | 37.21 | 7.33 | 47.15 | 12.16 | 344.84 |
| DP038140 | 3.42 | 28.17 | 116.57 | 35.93 | 45.73 | 14.12 | 12.38 | 40.83 | 5.56 | 33.34 | 7.57 | 24.39 | 8.46 | 62.04 | 41.71 | 316.34 |
| DP038354 | 2.20 | 16.25 | 38.98 | 31.96 | 65.94 | 23.62 | 9.97 | 50.39 | 6.60 | 4.41 | 3.58 | 44.43 | 8.80 | 185.40 | 29.95 | 5694.60 |
| DP017770 | 0.14 | 33.68 | 8.20 | 10.92 | 37.80 | 5.26 | 0.00 | 42.75 | 7.61 | 0.53 | 1.48 | 2194.20 | 3.40 | 56.29 | 11.16 | 394.67 |
| DP005144 | 0.68 | 20.59 | 23.61 | 14.90 | 48.67 | 4.54 | 21.97 | 47.44 | 7.53 | 2.96 | 1.75 | 115.87 | 11.91 | 126.84 | 133.08 | 863.09 |
| DP004716 | 0.13 | 6.70 | 3.37 | 17.25 | 28.73 | 0.00 | 7.56 | 28.05 | 3.82 | 1.28 | 1.97 | 316.98 | 1.16 | 80.73 | 8.06 | 975.12 |
| DP037177 | 1.28 | 9.08 | 46.60 | 22.00 | 50.13 | 7.63 | 1.71 | 23.96 | 5.19 | 7.63 | 3.27 | 113.64 | 2.40 | 86.82 | 14.37 | 35478.36 |

| Uncategorized | Innate Inflammation | | Cellular inflammation | | | | | Humoral inflammation | | | | NFkB-dependent | | IRF-dependent |
|---|---|---|---|---|---|---|---|---|---|---|---|---|---|---|
| | IL-1b | IL-6 | TNFa | IL-12p70 | IFNg | IL-2 | IL-15 | IL-17 | IL-4 | IL-5 | IL-13 | IL-9 | MIP-1a | MIP-1b | MCP-1 | IP-10 |
| DP000757 | 0.00 | 13.50 | 0.00 | 0.00 | 12.50 | 0.00 | 0.00 | 9.24 | 1.69 | 0.00 | 0.60 | 7.60 | 1.24 | 23.27 | 12.89 | 951.82 |
| DP009853 | 0.00 | 4.55 | 0.00 | 1.83 | 13.62 | 0.00 | 0.00 | 22.21 | 1.38 | 0.00 | 0.03 | 22.79 | 0.00 | 48.23 | 14.22 | 1025.12 |
| DP077232 | 0.00 | 9.78 | 0.00 | 0.94 | 0.00 | 0.00 | 3.25 | 14.08 | 1.56 | 1.62 | 0.52 | 5.87 | 2.13 | 53.79 | 42.49 | 996.39 |
| DP004288 | 0.16 | 0.98 | 3.37 | 6.09 | 8.97 | 0.00 | 1.05 | 30.29 | 3.40 | 1.01 | 3.00 | 0.00 | 0.25 | 15.59 | 1.80 | 636.54 |
| DP037073 | 0.21 | 2.70 | 0.52 | 3.67 | 18.43 | 0.00 | 0.33 | 0.00 | 3.43 | 1.01 | 0.83 | 0.00 | 0.00 | 44.73 | 0.00 | 687.97 |
| DP036642 | 0.24 | 14.09 | 0.96 | 2.78 | 8.97 | 0.00 | 2.23 | 26.14 | 2.62 | 1.46 | 0.63 | 8.22 | 0.61 | 54.37 | 18.13 | 532.45 |
| DP022522 | 0.00 | 3.74 | 0.00 | 2.45 | 27.64 | 0.00 | 0.00 | 0.00 | 2.04 | 0.43 | 0.00 | 0.00 | 0.00 | 27.27 | 19.56 | 835.17 |
| DP049910 | 0.27 | 1.40 | 5.44 | 5.59 | 7.25 | 0.00 | 0.02 | 32.78 | 3.55 | 1.10 | 0.90 | 0.00 | 1.38 | 111.16 | 24.36 | 3708.69 |
| DP042092 | 0.10 | 1.99 | 0.00 | 15.66 | 14.57 | 0.00 | 5.55 | 61.43 | 1.92 | 2.86 | 2.57 | 8.18 | 1.22 | 30.01 | 11.21 | 107.03 |
| DP022492 | 0.00 | 1.73 | 0.00 | 3.59 | 13.21 | 0.68 | 0.00 | 22.16 | 2.58 | 1.20 | 1.91 | 11.15 | 1.79 | 83.00 | 34.92 | 313.67 |
| DP038889 | 0.00 | 2.21 | 0.00 | 3.01 | 23.74 | 0.00 | 0.00 | 33.63 | 6.67 | 1.28 | 0.86 | 11.01 | 1.12 | 93.04 | 35.32 | 400.88 |
| DP035467 | 0.26 | 8.52 | 4.83 | 1.85 | 56.59 | 0.00 | 0.00 | 53.63 | 6.00 | 0.72 | 2.57 | 21.63 | 0.76 | 57.70 | 19.52 | 408.26 |
| DP009211 | 0.00 | 0.37 | 0.00 | 0.00 | 18.65 | 0.00 | 0.00 | 52.62 | 6.88 | 0.00 | 0.00 | 2.96 | 0.00 | 74.66 | 12.60 | 1501.65 |
| DP026651 | 0.44 | 1.05 | 8.59 | 8.25 | 30.51 | 0.00 | 0.00 | 22.30 | 5.54 | 1.86 | 1.03 | 4.59 | 0.00 | 125.32 | 5.40 | 3994.87 |
| DP079872 | 1.72 | 11.75 | 28.88 | 24.44 | 64.00 | 4.27 | 1.49 | 32.02 | 6.43 | 3.30 | 4.77 | 13.64 | 6.83 | 319.20 | 46.64 | 30319.28 |
| DP048626 | 0.78 | 4.81 | 12.24 | 15.66 | 39.80 | 1.14 | 0.00 | 30.22 | 4.82 | 3.62 | 2.74 | 14.51 | 1.93 | 69.13 | 15.99 | 459.38 |
| DP078913 | 1.56 | 3.13 | 14.27 | 21.16 | 41.68 | 0.00 | 0.00 | 27.71 | 5.58 | 2.09 | 2.49 | 12.33 | 6.39 | 50.19 | 16.14 | 1295.15 |
| DP099072 | 1.84 | 9.39 | 26.59 | 18.25 | 46.53 | 1.20 | 0.00 | 34.58 | 5.89 | 3.56 | 4.18 | 9.32 | 6.04 | 197.79 | 29.09 | 22900.79 |
| DP008461 | 1.44 | 6.43 | 18.42 | 16.62 | 30.03 | 0.00 | 0.00 | 47.06 | 5.46 | 3.65 | 3.91 | 8.32 | 5.59 | 35.04 | 18.20 | 681.26 |
| DP054511 | 0.84 | 4.55 | 16.68 | 11.61 | 13.46 | 1.61 | 3.33 | 56.57 | 4.44 | 2.86 | 2.27 | 4.80 | 3.13 | 91.71 | 36.21 | 438.76 |
| DP026334 | 0.62 | 7.69 | 4.39 | 13.76 | 31.29 | 6.24 | 8.48 | 71.34 | 2.53 | 2.96 | 8.88 | 18.99 | 1.39 | 54.68 | 6.37 | 4323.19 |
| DP007819 | 0.53 | 6.59 | 5.59 | 8.61 | 15.86 | 0.00 | 2.94 | 75.52 | 1.57 | 0.89 | 1.75 | 19.79 | 4.04 | 99.49 | 23.06 | 2163.56 |
| DP097512 | 0.93 | 5.93 | 21.43 | 16.72 | 24.52 | 1.07 | 6.73 | 78.91 | 4.69 | 3.81 | 2.90 | 13.52 | 3.07 | 63.77 | 15.64 | 593.64 |
| DP078432 | 0.58 | 2.81 | 7.05 | 8.02 | 21.36 | 0.00 | 1.27 | 65.72 | 4.36 | 2.51 | 1.57 | 12.62 | 4.60 | 182.95 | 12.84 | 3750.84 |
| DP041996 | 0.94 | 5.52 | 13.19 | 11.02 | 34.07 | 3.00 | 4.98 | 63.28 | 6.35 | 2.12 | 1.90 | 16.13 | 4.01 | 170.42 | 12.69 | 9745.31 |
| DP147705 | 0.61 | 4.60 | 11.81 | 5.92 | 41.68 | 0.00 | 0.00 | 25.52 | 6.68 | 0.98 | 1.22 | 35.81 | 4.00 | 103.19 | 103.13 | 1288.33 |

BIOMARKERS FOR THE IDENTIFICATION OF LIVER DAMAGE

RELATED APPLICATIONS

The present application is a National Stage application filed under Rule 371 based upon PCT/US2013/066674 filed Oct. 24, 2013 which claims priority to U.S. Provisional Application No. 61/717,977, filed Oct. 24, 2012, the entire disclosure of which is incorporated herein by reference.

TECHNICAL FIELD

The presently disclosed invention relates generally to the use of immune analytes as biomarkers for identifying liver damage in a mammal and/or predicting the survivability of a mammal suffering from liver damage.

BACKGROUND OF THE INVENTION

Liver injury caused by drugs and chemicals is a problem that continues to grow in prevalence and importance. Drug induced liver injury (DILI) is a common cause of acute liver failure in the United States, accounting for about 13% of such cases (1-3). DILI is also the most frequent adverse drug event that leads to the abandonment of otherwise promising new drug candidates or to the withdrawal from the market of new drugs, often after only months of use. Such occurrences have obvious and major human costs, in terms of pain, suffering, and death experienced by those who develop DILI, but also major economic costs to the companies that have developed these drugs, to their shareholders, and to society at-large because the resources that went into development of such doomed drugs might have been better spent on other measures to improve our health and well-being (4-7).

The prevalence of DILI is compounded by the growing use of herbal remedies and dietary supplements (HDS). These are often assumed to be safe because they are "natural." However, it is clear that many of these may cause serious liver injury. In recent years, about 10% of DILI instances in the U.S. have involved HDS (10), and even higher frequencies have been reported in the Far East (11).

In addition to DILI, the liver of a mammal can be damaged in a variety of other ways, including inflammation due to a viral infection (e.g., Hepatitis A, B, C, or E), obstruction of bile flow, accumulation of cholesterol or triglycerides, and compromised blood flow to the liver.

Regardless of its etiology, liver damage can be hard to diagnose. Commonly used biomarkers for liver damage, such as serum aminotransferases, alkaline phosphatase, and other enzymes, have limited sensitivity and specificity (7,9). Furthermore, providing an accurate prognosis for liver damage is even more difficult. For patients suffering from acute liver failure, there are no reliable tests to predict whether a liver transplant will be necessary in the near term (e.g., a six month time frame). Because of the limited supply of livers for transplant surgery, it is critically important to distinguish between patients that will require a transplant in the near term and patients that will not.

Accordingly, there remains an urgent need for methods and kits for accurately detecting liver damage and predicting the survivability of subjects suffering from life-threatening liver damage within a given time-frame.

BRIEF SUMMARY OF THE INVENTION

The present invention provides methods of characterizing liver injury in an individual, such as a mammal (e.g., a human). The methods can be used, for example, to distinguish between individuals experiencing life-threatening liver damage and those experiencing non-life-threatening liver damage. The methods can also be used to monitor individuals at risk of liver damage (e.g., due to DILI, viral hepatitis, autoimmune hepatitis, ischemic hepatitis, etc.) and to determine whether such individuals are likely to experience life-threatening liver failure and need a liver transplant within a particular time frame. The invention is based, among other things, on the successful identification of immunological markers (i.e., immune analytes and serum albumin) that exhibit coordinated changes in their blood concentration levels that correlate with increased risk of life-threatening liver damage.

Accordingly, in one aspect, the present invention provides methods of characterizing liver damage in an individual. In certain embodiments, the methods comprise directly or indirectly obtaining a concentration of serum albumin in a blood sample from the individual. The obtained serum albumin concentration is then compared with a predetermined concentration of serum albumin (e.g., 3.5 g/dL, 3.2 g/dL, or 2.8 g/dL). In certain embodiments, the methods comprise directly or indirectly obtaining the concentration(s) of one or more immune analytes selected from the group consisting of TNFα, IL-12, IL-17, IL-4, IL-5, IL-13, IL-9, MIP-1β, RANTES, FGF b, PDGF-bb, and IL-6 in a blood sample from the individual. The concentrations of the one or more immune analytes thus obtained are then compared to the concentrations of the same immune analytes found in the blood of healthy individuals (e.g., individuals that have healthy livers). In certain embodiments, the individual is identified as having life-threatening liver damage if (1) the individual's serum albumin concentration is less than or equal to the predetermined concentration of serum albumin (e.g., 2.8 g/dL), and (2) the concentrations of the one or more immune analytes in the individual's blood is less than the median concentrations of the corresponding immune analytes in the blood of healthy individuals (for IL-6, however, the applicable condition is a concentration in the individual's blood greater than the median concentration of IL-6 in the blood of healthy individuals). In certain embodiments, the individual is identified as having non-life-threatening liver damage if the individual's serum albumin concentration is greater than the predetermined concentration of serum albumin (e.g., 2.8 g/dL) and/or at least one of the obtained immune analyte concentrations in the individual's blood is not less than the median concentration of the corresponding immune analyte in the blood of healthy individuals (for IL-6, however, the applicable condition is a concentration in the individual's blood that is not greater than the median concentration of IL-6 in the blood of healthy individuals).

In certain embodiments, the methods further comprise informing the individual that s/he has been identified as having life-threatening liver damage. In other embodiments, the methods further comprise informing the individual that s/he has been identified as having non-life-threatening liver damage. In certain embodiments, the methods further comprise providing medical care for the individual that is consistent with the individual's identification status (i.e., having life-threatening or non-life-threatening liver damage). For example, in certain embodiments, the methods further comprise the step of prescribing a corticosteroid (e.g., prednisone) to the individual if the individual is identified as having life-threatening liver damage. In other embodiments, the methods further comprise the step of recommending a liver transplant procedure for the individual if the individual is identified as having life-threatening liver damage. In certain embodiments, the methods further comprising the step of performing a liver transplant for the individual if the individual is identified as having life-threatening liver damage.

The blood sample employed in the methods of the invention can be a serum sample. Alternatively, the blood sample can be a plasma sample. In general, the concentrations of immune analytes determined for the individual should be compared to concentrations (e.g., median concentrations) determined from samples of the same type (e.g., the concentration of IL-17 in the individuals serum should be compared with the median concentration of IL-17 detected in serum samples from healthy individuals). In preferred embodiments, the individual is a mammal, such as a human.

In preferred embodiments, directly or indirectly obtaining the concentration(s) of one or more immune analytes comprises obtaining the concentrations of at least three, and more preferably four, immune analytes selected from the group consisting of: TNFα, IL-12, IL-17, IL-4, IL-5, IL-13, IL-9, MIP-1β, RANTES, FGF b, PDGF-bb, and IL-6. Preferably, the methods comprise obtaining a concentration for IL-17, RANTES, and/or PDGF bb. Preferably, the methods comprise obtaining concentrations for IL-17, RANTES, and/or PDGF bb and at least one additional immune analyte selected from the group consisting of IL-4, IL-13, IL-9, and FGF b. In certain embodiments, the methods comprise obtaining concentrations for IL-17, RANTES, and/or PDGF bb and both TNFα and FGF b. Any of the forgoing methods can further comprise obtaining a concentration for IL-6 in the blood sample from the individual. As discussed elsewhere herein, an IL-6 concentration greater than the median concentration of IL-6 in healthy individuals is consistent with the individual having life-threatening liver damage.

In a related aspect, the invention provides methods of assessing liver damage in a subject enrolled in a clinical trial. The methods can be performed in the manner of the methods of characterizing liver damage in an individual, as described above and elsewhere herein. In certain embodiments, however, the methods of assessing liver damage in a subject enrolled in a clinical trial include the step of identifying the subject as having life-threatening liver damage, non-life-threatening liver damage, or normal liver function. Life-threatening liver damage and non-life-threatening liver damage are identified as described above and elsewhere herein. Normal liver function can be identified, for example, if (i) the serum albumin concentration value obtained from the subject's blood sample is greater than a predetermined concentration of serum albumin (e.g., 2.8 g/dL, 3.2 g/dL, or 3.5 g/dL), and (ii) all of the one or more immune analyte concentrations obtained from the subject's blood sample are greater than or equal to the median concentrations of the corresponding immune analytes in the blood of healthy subjects (for IL-6, however, the applicable condition is a concentration in the individual's blood less than or equal to the median concentration of IL-6 in the blood of healthy individuals).

In certain embodiments, the subject is a mammal, such as a human. In certain embodiments, the clinical trial is for a new drug (e.g., an anti-cancer drug or an anti-inflammatory drug). In certain embodiments, the subject is at risk for DILI.

In another aspect, the invention provides methods of assessing the survivability of an individual suffering from liver damage. Typically, the individual is a mammal, such as a human. In certain embodiments, the methods include obtaining, either directly or indirectly, the concentration of serum albumin in a blood sample (e.g., a serum sample) from the individual. In certain embodiments, the methods involve obtaining, either directly or indirectly, the concentrations of one or more immune analytes selected from the group consisting of TNFα, IL-12, IL-17, IL-4, IL-5, IL-13, IL-9, MIP-1β, RANTES, FGF b, PDGF-bb, and IL-6 in a blood sample (e.g., a serum sample) from the individual. After obtaining the concentrations of the immune analytes of interest, the values are compared, on an individual basis, with the median concentrations of corresponding immune analytes found in the blood of healthy individuals (e.g., individuals that have a healthy liver). In accordance with certain embodiments of the present invention, the methods include the step of determining if any of the one or more immune analyte concentrations obtained from the patient's blood sample is less than the corresponding median concentration of the immune analytes from healthy individuals (for IL-6, however, the applicable condition is a concentration in the individual's blood greater than the median concentration of IL-6 in the blood of healthy individuals). In addition to comparing the measured values of the immune analytes of interest, the concentration of serum albumin obtained from the individual's blood sample is compared to a predetermined concentration range or cutoff value (e.g., 2-5 g/dL, 2-4 g/dL, 2-3 g/dL, 2.5-3 g/dL, or 2.8 g/dL), and a determination is made as to whether the individual's serum albumin concentration is (i) less than the concentration range (or less than or equal to the predetermined cutoff value, or (ii) within the concentration range (or greater than the predetermined cutoff value).

In certain embodiments, the methods include a step of identifying the individual as having either a high likelihood of survival from liver damage (e.g., 90% or greater chance of survival for the next six months) or a high likelihood of mortality from liver damage (e.g., 90% or greater chance of dying within the next six months unless a liver transplant is performed). The identification can be completed based on the analysis and comparison of the measured immune analyte concentrations and serum albumin concentration. For instance, the individual can be identified as having a high likelihood of survival from liver damage when the measured serum albumin concentration value from the sample is greater than the predetermined cut off value (e.g., 2.8 g/dL) or when any of the one or more immune analyte concentrations obtained from the individual is greater than or equal to the median concentrations of the corresponding immune analytes found in the blood of healthy individuals (for IL-6, however, the applicable condition is a concentration in the individual's blood less than or equal to the median concentration of IL-6 in the blood of healthy individuals). Conversely, the individual can be identified as having a high likelihood of mortality from liver damage when the serum albumin concentration obtained from the individual is less than or equal to a predetermined cutoff value (e.g., 2.8 g/dL) and when all of the one or more immune analyte concentrations obtained from the individual are less than the median concentrations of the corresponding immune analytes found in the blood of healthy individuals (for IL-6, however, the applicable condition is a concentration in the individual's blood greater than the median concentration of IL-6 in the blood of healthy individuals).

In another aspect, the present invention provides methods of prioritizing a plurality of patients, including a first patient and a second patient, for receiving a liver transplant. In this regard, patients having a more immediate need for a liver transplant can be prioritized over patients that may not need a liver transplant at all (or at least have a less urgent need for a liver transplant). In accordance with certain embodiments of the present invention, a respective blood sample is received from a plurality of individuals suffering (or believed to be suffering) from liver damage. For each sample, the concentration value for serum albumin is obtained (e.g., measured by an appropriate assay) and the respective concentration values for one or more immune analytes selected from the group consisting of TNFα, IL-12, IL-17, IL-4, IL-5, IL-13, IL-9, MIP-1β, RANTES, FGF b, PDGF-bb, and IL-6 are obtained (e.g., assayed).

The immune analyte concentrations obtained from the first individual can be compared with the median concentrations of corresponding immune analytes found in the blood of healthy individuals to determine if any of the one or more immune analyte concentrations of the individual is less than the median concentration of the corresponding immune analyte found in the blood of healthy individuals (for IL-6, however, the applicable condition is a concentration in the individual's blood greater than the median concentration of IL-6 in the blood of healthy individuals). Similarly, the immune analyte concentrations obtained from the second individual can be compared with the median concentrations of corresponding immune analytes found in the blood of healthy individuals to determine if any of the one or more immune analyte concentrations of the individual is less than the median concentration of the corresponding immune analyte found in the blood of healthy individuals (again, for IL-6 the applicable condition is a concentration in the individual's blood greater than the median concentration of IL-6 in the blood of healthy individuals).

In certain embodiments, the methods include the step of determining one of the following: (i) that the first individual's sample has a serum albumin concentration value greater than a predetermined range or cutoff value (e.g., 2.8 g/dL), or (ii) any of the one or more immune analyte concentrations from the first individual's sample is greater than or equal to the median concentration of the corresponding immune analyte in the blood of healthy individuals (for IL-6, however, the applicable condition is a concentration in the individual's blood less than or equal to the median concentration of IL-6 in the blood of healthy individuals). In certain embodiments, the methods include the step of determining one of the following: (i) that the second individual's sample has a serum albumin concentration value that is less than a predetermined range (e.g., 2.5-3.0 g/dL) or less than or equal to a predetermined cutoff value (e.g., 2.8 g/dL) and (ii) all of the one or more immune analyte concentrations from the second individual's sample are less than the median concentrations of the corresponding immune analytes found in the blood of healthy individuals (for IL-6, however, the applicable condition is a concentration in the individual's blood greater than the median concentration of IL-6 in the blood of healthy individuals). In accordance with certain embodiments of the present invention, a step of identifying the second individual as having a higher risk of mortality due to liver damage than the first individual can be performed. In certain embodiments, therefore, an additional step of providing a recommendation that a liver transplant be performed on the second individual before a liver transplant is performed on the first individual can be carried out. In this regard, the second individual is prioritized over the first individual for receiving a liver transplant.

In yet another aspect, the present invention provides kits that can be used to practice the methods of the invention. In certain embodiments, the kits can comprise (i) a first antibody suitable to detect and quantify serum albumin and/or an immune analyte selected from the group consisting of TNFα, IL-12, IL-17, IL-4, IL-5, IL-13, IL-9, MIP-1, RANTES, FGF b, PDGF-bb, and IL-6; and (ii) instructions for characterizing liver damage based on the concentrations of immune analytes and serum albumin in comparison to median concentrations of the corresponding immune analytes representative of individuals having a healthy liver and a predetermined range (e.g., 2.5-3.0 g/dL) or cut off value (e.g., 2.8 gL) for serum albumin, respectively. In certain embodiments, the instructions further comprise tables listing the median concentrations of immune analytes (e.g., TNFα, IL-12, IL-17, IL-4, IL-5, IL-13, IL-9, MIP-1β, RANTES, FGF b, PDGF-bb, IL-6) in individuals having a healthy liver.

In certain embodiments, the kits further comprise a second antibody suitable for detection of serum albumin and/or an immune analyte selected from the group consisting of TNFα, IL-12, IL-17, IL-4, IL-5, IL-13, IL-9, MIP-1β, RANTES, FGF b, PDGF-bb, and IL-6. In certain embodiments, the second antibody binds to the same immune analyte as the first antibody, but to a different epitope. In other embodiments, the second antibody binds to a different immune analyte than the first antibody.

In certain embodiments, the kits further comprise a second antibody and a third antibody, each suitable for detection of serum albumin and/or an immune analyte selected from the group consisting of TNFα, IL-12, IL-17, IL-4, IL-5, IL-13, IL-9, MIP-1β, RANTES, FGF b, PDGF-bb, and IL-6. In certain embodiments, the third antibody binds to the same immune analyte as the first or second antibody, but to a different epitope. In other embodiments, the third antibody binds to a different immune analyte than the first and second antibodies.

In certain embodiments, the kits further comprise a second antibody, a third antibody, and a fourth antibody, each suitable for detection of serum albumin and/or an immune analyte selected from the group consisting of TNFα, IL-12, IL-17, IL-4, IL-5, IL-13, IL-9, MIP-1β, RANTES, FGF b, PDGF-bb, and IL-6. In certain embodiments, the fourth antibody binds to the same immune analyte as the first antibody, the second antibody, or the third antibody, but to a different epitope. In other embodiments, the fourth antibody binds to a different immune analyte than the first, second, and third antibodies.

In certain embodiments, the first antibody of the kit binds to an immune analyte selected from the group consisting of IL-9, IL-17, RANTES, and PDGF-bb. In certain embodiments, the first and second antibodies of the kit bind to immune analytes selected from the group consisting of IL-9, IL-17, RANTES, and PDGF-bb. In certain embodiments, the first, second, and third antibodies of the kit bind to immune analytes selected from the group consisting of IL-9, IL-17, RANTES, and PDGF-bb. In certain embodiments, the first, second, third, and fourth antibodies of the kit bind to immune analytes selected from the group consisting of IL-9, IL-17, RANTES, and PDGF-bb.

In certain embodiments, at least one antibody (e.g., the first, second, third, or fourth antibody) is attached to a solid support. In certain embodiments, all of the antibodies are attached to a solid support. The solid support can provide a multiplex assay, such as would be suitable for detection and quantification of serum albumin and/or immune analytes (e.g., three or four analytes) selected from the group consisting of TNFα, IL-12, IL-17, IL-4, IL-5, IL-13, IL-9, MIP-1β, RANTES, FGF b, PDGF-bb, and IL-6. In certain embodiments, the multiplex assay detects and quantifies each of IL-9, IL-17, RANTES, and PDGF-bb.

BRIEF DESCRIPTION OF THE SEVERAL VIEWS OF THE DRAWING(S)

Having thus described embodiments of the invention in general terms, reference will now be made to the accompanying drawings, which are not necessarily to scale, and wherein:

FIG. 5 illustrates profiles of immune analytes in serum at onset of DILI;

FIG. 6 illustrates profiles of cytokines in sera of DILI subjects at 6-month follow-up; and FIG. 7 illustrates profiles of chemokines in sera of DILI subjects at DILI onset.

DETAILED DESCRIPTION

Figure 1:
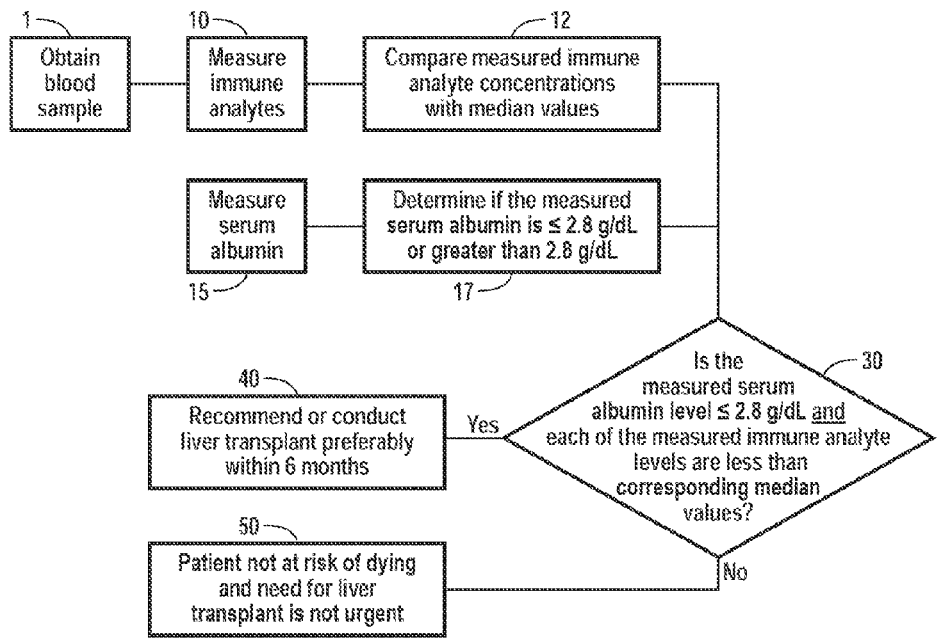
FIG. 1 illustrates methods according to certain embodiments of the present invention.

The present invention now will be described more fully hereinafter with reference to the accompanying drawings, in which some, but not all embodiments of the inventions are shown. Indeed, this invention can be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

In its most general form, the present invention is directed to methods of characterizing liver damage in an individual. The origin of the liver damage can e.g., viral hepatitis, ischemic hepatitis, autoimmune hepatitis, DILI, or a metabolic disease that causes liver failure. Thus, in certain embodiments, the origin of the liver damage is DILI. In some applications of the methods, however, the origin of the liver damage is unknown. The liver damage can be life-threatening liver damage, or non-life threatening liver damage. As used herein, the term "life-threatening liver damage" refers to liver damage that, if not treated, has a high probability of resulting in death within a defined time frame. As used herein, the term "non-life threatening liver damage" refers to liver damage that, if not treated, has a low probability of resulting in death with a defined time frame. A high probability is greater than 70% (e.g., at least 75%, 80%, 85%, 90%, 95%, or more). A low probability is less than 30% (e.g., no more than 25%, 20%, 15%, 10%, 5%, or less). A defined time frame can be, for example, several months (e.g., 3 months, 6 months, 9 months, 1 year), but is preferably 6 months. The terms "liver damage," as used herein, includes liver failure (e.g., acute liver failure and sub-acute liver failure).

The steps in the methods of characterizing liver damage in an individual can be applied in various contexts. Thus, the invention encompasses methods of assessing liver damage in a subject participating in a clinical trial, methods of assessing the survivability of an individual suffering from liver damage, and methods of prioritizing one or more patients in a plurality of patients for receiving a liver transplant. Each of the methods involves analyzing concentration levels of particular immune analytes identified as biomarkers associated with acute liver. The immune analyte biomarkers employed can be selected from TNFα, IL-12, IL-17, IL-4, IL-5, IL-13, IL-9, MIP-1β, RANTES, FGF b, PDGF-bb, IL-6, and any combination thereof. In addition to analysis of certain immune analyte biomarkers, a patient's serum albumin concentration level can also be evaluated relative to a predetermined range (e.g., 2-5 g/dL, 2-4 g/dL, 2-3 g/dL, 2.5-3 g/dL) or cut off value (e.g., 3.5 g/dL, 3.2 g/dL, or 2.8 g/dL) for serum albumin associated with liver damage. In certain embodiments, the predetermined serum albumin range is 2.5-3.0 g/dL. In certain preferred embodiments, the predetermined serum albumin cutoff value is 2.8 g/dL. Selection of the predetermined serum albumin range or cutoff value can be made based on considerations of the associated rates of false positives and false negatives.

The concentration values of the immune analytes and/or serum albumin can be indirectly or directly obtained. In certain embodiments, "indirectly obtained" refers to obtaining the concentration value from a third party, such as a diagnostic company, whereas "directly obtained" refers to obtaining the concentration by direct measurement (e.g., using an "in-house" lab). The immune analytes can be obtained by measurement with an appropriate assay (e.g., a multi-plex assay designed or configured for detecting and/or quantifying the particular immune analytes of interest). Similarly, the concentration value of serum albumin from the sample can be obtained directly or indirectly as is well known in the art. Relevant assays include antibody-based assays (e.g., ELISA) and non-antibody-based assays (e.g., mass spectrometry). Alternatively, in certain embodiments, the immune analytes and/or serum albumin can be detected indirectly by measuring the expression of the corresponding mRNA (e.g., using PCR or any other suitable form of amplification). As persons skilled in the art will readily understand, use of indirect techniques such as PCR require a sample that contains sufficient mRNA and, preferably, the cells that secrete the analytes of interest (e.g., such as a tissue or whole blood sample).

After the respective concentration values of the particular immune analytes of interest have been obtained, these values can then be compared, on an individual basis, with the median concentrations of corresponding immune analytes found in the blood (e.g., serum or plasma) of healthy individuals (e.g., individuals that have a healthy liver). In accordance with certain embodiments of the present invention, a step of determining if any of the one or more of the immune analyte concentrations obtained (e.g, from a patient's blood sample) is less than the median concentration of a corresponding immune analyte from healthy individuals. In addition to comparing the measured values of the immune analytes of interest, the obtained concentration value of the serum albumin from a patient's blood sample is compared to a predetermined range (e.g., 2-5 g/dL, 2-4 g/dL, 2-3 g/dL, or 2.5-3 g/dL) or cutoff value (e.g., 3.5 g/dL, 3.2 g/dL, or 2.8 g/dL) and a determination of whether the serum albumin concentration value from the sample is (i) less than the predetermined range (or less than or equal to the predetermined cutoff value) or (ii) with in the predetermined range (or greater than the predetermined cutoff value).

In accordance with certain embodiments of the present invention, an individual is identified as having life-threatening liver damage if (1) the individual's serum albumin concentration is less than or equal to the preselected range (e.g., 2.5-3.0 g/dL) or cutoff value (e.g., 2.8 g/dL), and (2) the concentrations of the one or more immune analytes in the individual's blood are less than the median concentrations of corresponding immune analytes in the blood of healthy individuals (for IL-6, however, the applicable condition is a concentration in the individual's blood greater than the median concentration of IL-6 in the blood of healthy individuals). Alternatively, the individual is identified as having non-life-threatening liver damage if the individual's serum albumin concentration is within (or above) the preselected range (e.g., 2.5-3.0 g/dL) or greater than the preselected cutoff (e.g., 2.8 g/dL), and/or the immune analyte concentration(s) in the individual's blood are not all less than the median concentration(s) of the corresponding immune analyte from healthy individuals (for IL-6, however, the applicable condition is a concentration in the individual's blood not greater than the median concentration of IL-6 in the blood of healthy individuals). In accordance with other embodiments of the invention, an individual (e.g., a subject in a clinical trial) is identified as having normal liver function if (i) the serum albumin concentration value obtained from the subject's blood sample is within (or above) the preselected range (e.g., 3.0-4.0 g/dL or 3.5-5.0 g/dL) or greater than the preselected cutoff (e.g., 2.8 g/dL, 3.2 g/dL, or 3.5 g/dL), and (ii) all of the one or more immune analyte concentrations obtained from the subject's blood sample are greater than or equal to the median concentrations of the corresponding immune analytes from healthy subjects.

For methods of the invention involving the assessment of liver damage in a subject that is part of a clinical trial, the subject can be removed from the clinical trial if the subject is identified as having life-threatening liver damage. Similarly, the subject can be removed from the clinical trial if the subject is identified as having non-life threatening liver damage.

For subjects involved in clinical trials, there is a possibility of assessing liver damage at multiple time points during the clinical trial (e.g., prior to the clinical trial, right at the start of the trial, and at one or more time points during the trial). Thus, in certain embodiments, the assessment of liver damage is performed at least twice during the trial. Thus, the extent of liver damage (if any) can be tracked over the course of the trial. In certain embodiments, the subject is removed from the clinical trial because the subject's identification as having normal liver function changes to having non-life-threatening liver damage during the course of the trial. In certain embodiments, the subject is removed from the clinical trial because the subject's identification as having normal liver function changes to having life-threatening liver damage during the course of the trial. In other embodiments, the subject is removed from the clinical trial if the subject's identification as having non-life threatening liver damage changes to having life-threatening liver damage during the course of the trial.

In accordance with certain embodiments of the present invention, a step of identifying the patient as having either a high likelihood of survival from liver damage (e.g., 90% or greater chance of survival for the next six months) or a high likelihood of mortality (e.g., 90% or greater chance of dying within the next six months unless a liver transplant is performed) from liver damage can be completed based on the analysis and comparison of the measured immune analyte concentrations and serum albumin concentration. For instance, a patient can be identified as having a high likelihood of survival from liver damage when the measured serum albumin concentration value from the sample is greater than 2.8 g/dL or when any of the one or more measured immune analyte concentrations from the sample is less than the median concentration of the corresponding immune analyte found in the blood of healthy individuals.

Also, a patient can be identified as having a high likelihood of mortality from liver damage when the serum albumin concentration value obtained from the sample is less than or equal to 2.8 g/dL and when all of the one or more immune analyte concentrations from the sample are less than the median concentrations of the corresponding immune analytes found in the blood of healthy individuals.

In certain embodiments of the present invention, the immune analytes of interest comprise IL-17; RANTES; PDGF-bb; and FGF b. For instance, concentration values for each of IL-17; RANTES; PDGF-bb; and FGF b can be obtained (e.g., measured or assayed) and compared to given median concentration values representative of healthy individuals (e.g., healthy liver) for each of IL-17; RANTES; PDGF-bb; and FGF b. That is, the measured concentration value of IL-17 from the blood sample is compared to the given median concentration value of IL-17 representative of healthy individuals; the measured concentration value of RANTES from the blood sample is compared to the given median concentration value of RANTES representative of healthy individuals; and so forth. In certain embodiments, the only immune analytes for which concentration values are obtained from a patient's blood sample are IL-17; RANTES; PDGF-bb; and FGF b.

In certain embodiments of the present invention, the immune analytes of interest comprise IL-17; TNFa; RANTES and FGF b. For instance, concentration values for each of IL-17; TNFa; RANTES and FGF b can be obtained (e.g., measured or assayed) and compared to given median concentration values representative of healthy individuals (e.g., healthy liver) for each of IL-17; TNFa; RANTES and FGF b. That is, the measured concentration value of IL-17 from the blood sample is compared to the given median concentration value of IL-17 representative of healthy individuals; the measured concentration value of PGF b from the blood sample is compared to the given median concentration value of PGF b representative of healthy individuals; and so forth. In certain embodiments, the only immune analytes for which concentration values are obtained from a patient's blood sample are IL-17; TNFa; RANTES and FGF b.

In certain embodiments of the present invention, the immune analytes of interest comprise IL-17; PDGF bb; RANTES; and IL-4. For instance, concentration values for each of IL-17; PDGF bb; RANTES; and IL-4 can be obtained (e.g., measured or assayed) and compared to given median concentration values representative of healthy individuals (e.g., healthy liver) for each of IL-17; PDGF bb; RANTES; and IL-4. That is, the measured concentration value of IL-17 from the blood sample is compared to the given median concentration value of IL-17 representative of healthy individuals; the measured concentration value of IL-4 from the blood sample is compared to the given median concentration value of IL-4 representative of healthy individuals; and so forth. In certain embodiments, the only immune analytes for which concentration values are obtained from a patient's blood sample are IL-17; PDGF bb; RANTES; and IL-4.

In certain embodiments of the present invention, the immune analytes of interest comprise IL-17; PDGF bb; RANTES; and IL-13. For instance, concentration values for each of IL-17; PDGF bb; RANTES; and IL-13 can be obtained (e.g., measured or assayed) and compared to given median concentration values representative of healthy individuals (e.g., healthy liver) for each of IL-17; PDGF bb; RANTES; and IL-13. That is, the measured concentration value of IL-17 from the blood sample is compared to the given median concentration value of IL-17 representative of healthy individuals; the measured concentration value of IL-13 from the blood sample is compared to the given median concentration value of IL-13 representative of healthy individuals; and so forth. In certain embodiments, the only immune analytes for which concentration values are obtained from a patient's blood sample are IL-17; PDGF bb; RANTES; and IL-13.

In certain preferred embodiments of the present invention, the immune analytes of interest comprise IL-17; PDGF bb; RANTES; and IL-9. For instance, concentration values for each of IL-17; PDGF bb; RANTES; and IL-9 can be obtained (e.g., measured or assayed) and compared to given median concentration values representative of healthy individuals (e.g., healthy liver) for each of IL-17; PDGF bb; RANTES; and IL-9. That is, the measured concentration value of IL-17 from the blood sample is compared to the given median concentration value of IL-17 representative of healthy individuals; the measured concentration value of IL-9 from the blood sample is compared to the given median concentration value of IL-9 representative of healthy individuals; and so forth. In certain embodiments, the only immune analytes for which concentration values are obtained from a patient's blood sample are IL-17; PDGF bb; RANTES; and IL-9.

In one alternative embodiment, the immune analytes of interest comprise IL-17; RANTES; IL-9; and IL-6. For instance, concentration values for each of IL-17; RANTES; IL-9; and IL-6 can be obtained (e.g., measured or assayed) and compared to given median concentrations representative of healthy individuals (e.g., healthy liver) for each of IL-17; RANTES; IL-9; and IL-6. That is, the measured concentration value of IL-17 from the blood sample is compared to the given median concentration value of IL-17 representative of healthy individuals; the measured concentration value of IL-6 from the blood sample is compared to the given median concentration value of IL-6 representative of healthy individuals; and so forth. In certain embodiments, the only immune analytes for which concentration values are obtained from a patient's blood sample are IL-17; RANTES; IL-9; and IL-6. In these particular embodiments in which the immune analytes of interest either comprise or consist of IL-17; RANTES; IL-9; and IL-6, identification of a high likelihood of mortality is predicted or identified when (i) the measured concentration values of IL-17; RANTES; IL-9 in the patient's blood sample are less the median value representative of healthy individuals, (ii) the measured concentration value of IL-6 in the patient's blood sample is higher than the median value representative of healthy individuals; and the measured value of the serum albumin in the patient's blood sample is less than a predetermined range (e.g., 2-5 g/dL, 2-4 g/dL, 2-3 g/dL, or 2.5-3.0 g/dL) or less than or equal to a predetermined cutoff value (e.g., 3.5 g/dL, 3.2 g/dL, or 2.8 g/dL).

In accordance with certain embodiments, the methods can include an additional step of informing the individual/subject of the diagnosis (i.e., identification) and/or prescribing appropriate therapy. For individuals/subjects identified as having non-life-threatening liver damage, appropriate therapy can include supportive care, e.g., improved nutrition and maintenance of hydration and electrolytes. For individuals/subjects identified as having life-threatening liver damage, appropriate therapy can include prescribing medication (e.g., a corticosteroid, such as prednisone), and/or recommending a liver transplant procedure. Methods according to certain embodiment of the present invention can further comprise a step of performing a liver transplant for a patient after identifying that particular patient as having a high likelihood (e.g., greater than 90% chance of death within 6 months from the onset of liver damage) of mortality from liver damage unless a liver transplant is performed.

Methods in accordance with certain embodiments of the present invention can accurately predict or identify which patients (e.g., human or other mammal) have a high likelihood of mortality within 6 months from the onset of liver damage (e.g., DILI). For instance, methods according to embodiments of the present invention can identify or predict a high likelihood of death from liver damage for a patient, wherein the likelihood of death is about 80%-100% (e.g., 85%-99%, 90%-99%, or 95%-99%). That is, a determination or identification of a "high likelihood" of death from liver damage for a patient can comprise an accuracy of about 80%-100% (e.g., 85%-99%, 90%-99%, or 95-99%).

Similarly, methods in accordance with certain embodiments of the present invention can accurately predict or identify which patients (e.g., human or other mammal) have a high likelihood of survival beyond 6 months from the onset of liver damage. For instance, methods according to embodiments of the present invention can identify or predict a high likelihood of survival for a patient, wherein the likelihood of survival is about 80%-100% (e.g., 85%-99%, 90%-99%, or 95%-99%) chance of survival beyond 6 months from the onset of liver damage. That is, a determination or identification of a "high likelihood" of survival from liver damage for a patient can have an accuracy of about 80%-100% (e.g., 85%-99%, 90%-99%, or 95-99%).

FIG. 1 illustrates methods according to certain embodiments of the present invention. As shown in FIG. 1, an initial step can comprise a step of obtaining a blood sample 1 from a patient. The blood sample can be subjected to one or more analytical techniques to measure the respective concentrations of immune analytes of interest 10 and to measure the serum albumin concentration 15. In step 12, the measured respective concentrations of immune analytes of interest (e.g., IL-17; PDGF bb; RANTES; and IL-9) can be compared to median values for these particular analytes. Median values for immune analytes representative of healthy individuals can include the values provided in Table 1 (below).

TABLE 1

Median values for immune analytes for comparison to measured values of immune analytes from a blood sample.

| Immune Analytes | Median Values in Healthy Individuals | Range of Median Values in Healthy Individuals |
|---|---|---|
| TNFα | 17.1 | 10-25 |
| IL-12 | 15.7 | 8-23 |
| IL-17 | 45.2 | 35-55 |
| IL-4 | 5.6 | 2-10 |
| IL-5 | 3.0 | 1-8 |
| IL-13 | 2.7 | 1-8 |
| IL-9 | 13.6 | 5-20 |
| MIP-1β | 84.1 | 70-95 |
| RANTES | 2529.0 | 2400-2650 |
| FGF b | 10.9 | 5-17 |
| PDGF-bb | 4207.0 | 4100-4300 |

In step 17, the measured serum albumin concentration (from step 15) can be analyzed to determine if the measured concentration is less than or equal to the predetermined cutoff of 2.8 g/dL (according to these particular embodiments). Step 30 comprises determining if the measured serum albumin concentration in the sample is less than or equal to the predetermined cutoff of 2.8 g/dL (according to these particular embodiments) and if each of the measured immune analyte concentrations of interest are less than the corresponding median value representative of healthy individuals (e.g., having a healthy liver). If a determination is made that the measured concentration levels from the blood sample satisfy both requirements, then step 40 can be performed comprising providing a recommendation for a liver transplant, preferably with 6 months of the determination or within 6 months of the onset of liver damage (if ascertainable or known). In the event that the measured concentration levels do not satisfy either (or both) requirements, then step 50 can be performed comprising concluding that the patient is not at risk of dying within the next six months or within 6 months from the onset of liver disease (if known or ascertainable). Step 50 can further comprise a step of de-prioritizing the patient for a liver transplant.

Figure 2:
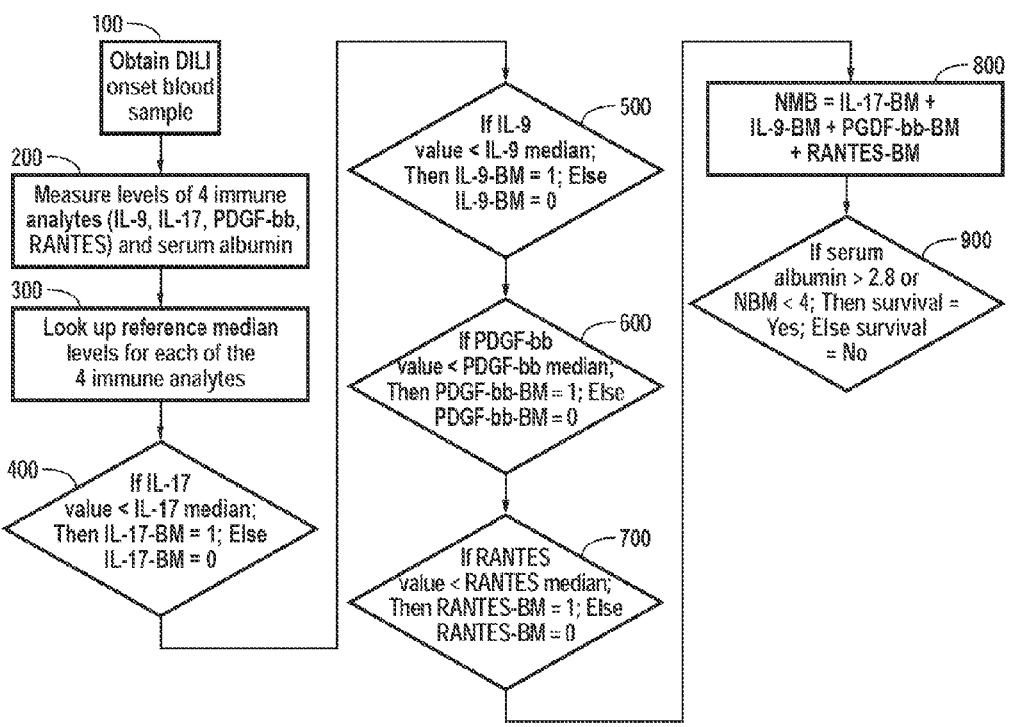
FIG. 2 illustrates one particular method according to certain embodiments of the present invention.

FIG. 2 illustrates certain preferred embodiments according to the present invention. In such embodiments, an initial step 100 comprising obtaining a blood sample from a patient is performed. The blood sample is subjected to step 200, comprising measuring the following four specific immune analytes: IL-17; PDGF bb; RANTES; and IL-9. In addition, the serum albumin concentration in the sample is obtained. Subsequently, step 300 comprising comparing the measured immune analyte concentrations to reference median concentration levels for each immune analyte is performed. In these particular embodiments shown in FIG. 2, each measured immune analyte is assigned a "Below Median" ("BM") value or either "1" or "0" depending on whether the measured concentration for a given immune analyte is less than the reference median concentration. Steps 400, 500, 600, and 700 comprise assigning a BM to each measured immune analyte of interest (i.e., step 400 for IL-17; step 500 for IL-9; step 600 for PDFGF bb; and step 700 for RANTES). Once a BM has been assigned for each immune analyte of interest, step 800 is performed in which a "Number Below Median" is calculated by adding all of the BM values together. For the embodiments illustrated in FIG. 2, the maximum NBM is four (4) since only four immune analytes were measured. Subsequently, step 900 is performed which comprises determining or predicting if the patient will survive or not survive based on the calculated NBM and measured concentration of serum albumin. For instance, if the measured serum albumin concentration is greater than 2.8 g/dL or the NBM is less than 4 (for these particular embodiments) then the patent will survive the liver damage, at least for 6 months from its onset. However, if the measured serum albumin concentration is not greater than 2.8 g/dL and the NBM equals 4 then the patient is not expected to survive the liver damage and will likely die within 6 months from its onset absent a liver transplant.

In another aspect, the present invention provides methods of prioritizing a plurality of patients, including a first patient and a second patient, for receiving a liver transplant. In this regard, patients in more immediate need for a liver transplant can be prioritized over patients that may not need a liver transplant at all, or at least have a less urgent need for a liver transplant. In accordance with certain embodiments of the present invention, a respective blood sample is received from a plurality of individuals suffering (or believed to be suffering) from liver damage. For each sample, the concentration value for serum albumin is obtained (e.g., measured by an appropriate assay) and the respective concentration values for one or more immune analytes selected from the group consisting of TNFα, IL-12, IL-17, IL-4, IL-5, IL-13, IL-9, MIP-1β, RANTES, FGF b, PDGF-bb, and IL-6 is obtained (e.g., assayed). The obtained immune analyte concentration values from the first individual can be compared with the corresponding median immune analyte concentrations from healthy individuals to determine if any of the one or more immune analyte concentrations measured from the sample is less than the corresponding median immune analyte concentrations from healthy individuals. Similarly, the obtained immune analyte concentration values from the second individual can be compared with the corresponding median immune analyte concentrations from healthy individuals to determine if any of the one or more immune analyte concentrations measured from the sample is less than the corresponding median immune analyte concentrations from healthy individuals. Next, a step is performed for determining one of the following: (i) that the first individual's sample has a serum albumin concentration value greater than a predetermined cutoff value (e.g., 2.8 g/dL) or (ii) any of the one or more immune analyte concentrations from the first individual's sample is less than the corresponding median immune analyte concentrations from healthy individuals. With regard to the second individual, a step is performed for determining one of the following: (i) that the second individual's sample has a serum albumin concentration value that is less than or equal to a predetermined cutoff value (e.g., 2.8 g/dL) and (ii) all of the one or more immune analyte concentrations from the second individual's sample is less than the corresponding median immune analyte concentrations from healthy individuals. In accordance with certain embodiments of the present invention, a step of identifying the second individual as having a higher risk of mortality due to liver damage than the first individual can be performed. In certain embodiments, therefore, an additional step of providing a recommendation that a liver transplant be performed on the second individual before a liver transplant is performed on the first individual can be carried out. In this regard, the second individual is prioritized over the first individual for receiving a liver transplant. Preferably, the liver transplant procedure is performed on the second individual within 6 months from the onset of liver damage (if known or ascertainable) or from the date of identifying the second individual as having a higher risk of mortality due to liver damage Methods of prioritizing a plurality of patients for receiving a liver transplant according to certain embodiments of the present invention can comprises analysis of any specific grouping of immune analytes disclosed herein. For each sample, by way of example, the concentration values for IL-9, IL-17, RANTES, and PDGF-bb; IL-17, RANTES, PDGF-bb, and FGF b; IL-17, TNFα, RANTES, and FGF b; IL-17, PDGF bb, RANTES, and IL-4; and IL-17, PDGF bb, RANTES, and IL-13 can be utilized as previously discussed.

In yet another aspect, the present invention provides kits that can be used to characterize liver damage. In some embodiments, the kits are used to assess liver damage in subjects taking part in a clinical trial. In other embodiments, the kits are used to predict or identify which patients will survive or die (in the absence of a liver transplant) from liver damage. These kits can also aid in the prioritization of a plurality of patients for receiving a liver transplant. According to certain embodiments of the present invention, the kits can comprise (i) at least one antibody-based assay configured to detect and/or quantify immune analytes selected from the group consisting of TNFα, IL-12, IL-17, IL-4, IL-5, IL-13, IL-9, MIP-1β, RANTES, FGF b, PDGF-bb, and IL-6, and (ii) instructions for carrying out any of the methods disclosed herein (e.g., identifying the survivability of an individual suffering from liver damage based on the concentration of serum albumin in a blood sample from the individual, as compared to a range or cutoff value (e.g., 2.8 g/dL), and the concentration values of measured immune analytes in the blood sample as compared to median concentration values representative of individuals having a healthy liver). In certain preferred embodiments, the at least one antibody-based assay comprises a multiplex assay configured to simultaneously detect and/or quantify immune analytes selected from the group consisting of TNFα, IL-12, IL-17, IL-4, IL-5, IL-13, IL-9, MIP-1β, RANTES, FGF b, PDGF-bb, and IL-6.

Kits according to certain embodiments of the present invention can comprises one or more antibody-based assays configured to detect and/or quantify immune analytes of any specific grouping of immune analytes disclosed herein. For each sample, by way of example, the one or more antibody-based assays can be configured to specifically detect and/or quantify any of the following specific groups of immune analytes: IL-9, IL-17, RANTES, and PDGF-bb; IL-17, RANTES, PDGF-bb, and FGF b; IL-17, TNFα, RANTES, and FGF b; IL-17, PDGF bb, RANTES, and IL-4; and IL-17, PDGF bb, RANTES, and IL-13.

In certain preferred embodiments, the at least one antibody-based assay detects and quantifies immune analytes selected from the group consisting of: IL-9; IL-17; RANTES; and PDGF-bb. More preferably, the at least one antibody-based assay detects and quantifies each of IL-9; IL-17; RANTES; and PDGF-bb. In certain preferred embodiments, the at least one anti-body based assay comprises a multiplex assay configured to simultaneously detect and/or quantify each of IL-9; IL-17; RANTES; and PDGF-bb.

Kits according to certain embodiments of the present invention can also comprise tables listing the median concentration of each immune analyte of interest in individuals having a healthy liver. For example, the instructions can include any of the values provided in Table 1.

EXAMPLES

Certain embodiments of the present invention are further illustrated by the following working study, which in no way should be construed as being further limiting. That is, the specific methods and results described are illustrative of certain embodiments, including a preferred embodiment, of the present invention, not limiting.

A study was conducted in which levels of 27 immune analytes were measured in the sera of subjects with well-characterized, carefully studied, acute DILI, who were then followed for at least one year in the prospective US Drug-Induced Liver Injury Network. This Network and its major methods have been described previously (10, 25, 26), and findings in the first three hundred subjects enrolled have been described (10). In this work, results were compared from 78 subjects with acute DILI, with those of 40 normal controls (e.g., volunteer blood donors having a healthy liver) in whom serum proteomic profiles were reported recently (27). As discussed below, striking changes in innate and adaptive cellular responses were observed, and a new means for early prediction of outcomes has been developed, based upon results at initial acute presentation for four serum immune analytes (interleukin 9, interleukin 17, platelet derived growth factor bb, and RANTES) and the level of the serum albumin in accordance with certain embodiments of the present invention.

Subjects Studied

Serum samples from subjects with DILI were collected as part of the Drug Induced Liver Injury Network (DILIN) prospective study, in which subjects with suspected DILI were enrolled and detailed clinical data were collected (25). The subjects with DILI studied in this work were all 78 subjects with acute DILI (e.g., onset two weeks or less prior to enrollment) enrolled between December 2004 and July 2010, as recently described by Bell et al (27). Clinical data were reviewed by the DILIN Causality Committee, which made the final determination as to whether the case qualified as bona fide DILI, and assigned each implicated drug a probability of having caused DILI (26). Types of liver injury and R values were as described (10, 27). Whenever possible, subjects were followed for at least 6 months to assess whether there was recovery or evidence of development of chronic DILI. Blood samples were collected and sent to the central DILIN sample repository for processing and storage at −80° C. Sera from healthy controls (volunteer blood donors) were obtained from a blood bank (27).

Inclusion/Exclusion Criteria

Adults and children, older than 2 years of age, with documented clinically significant DILI as evidenced by any of the following criteria were included in the DILIN prospective study: 1) jaundice or serum bilirubin>2.5 mg/dL, and any elevations in ALT, AST, or alkaline phosphatase; 2) no jaundice and serum bilirubin<2.5 mg/dL, but two or more elevations in serum ALT or AST (>5×ULN) or elevations in serum alkaline phosphatase (>2×ULN); and 3) elevations in serum ALT or AST>5× baseline values or elevations in serum alkaline phosphatase>2× baseline values in persons with known preexisting liver disease. Subjects were excluded on the following basis: 1) other known causes of acute liver injury, such as acute cholangitis, acute viral hepatitis, or autoimmune liver disease; 2) acetaminophen hepatotoxicity; and 3) liver transplantation prior to the onset of DILI, 4) failure to give informed consent, or inability or unwillingness to comply with case ascertainment procedures.

Immune Analyte Profiling by Bio-Plex Assay

Concentrations of immune analytes in sera were determined using a human 27-plex assay [14 cytokines (IL-1β, IL-1ra, IL-2, IL-4, IL-5, IL-6, IL-9, IL-10, IL-12, IL-13, IL-15, IL-17, IFN-γ, TNF-α); 7 chemokines (Eotaxin, IL-8, IP-10, MCP-1, MIP— 1α, MIP-1β, RANTES); and 6 growth factors (IL-7, FGF basic, G-CSF, GM-CSF, PDGF-BB, VEGF)] and measured with a Bio-Plex Suspension Array System provided by Bio-Rad (Hercules, Calif., USA).

Sera from DILI subjects (at onset and 6 month follow-up) and healthy controls were processed and analyzed according to manufacturer's instructions. Briefly, samples were diluted 1:4 (v:v) in sample diluent and incubated for 30 minutes (room temperature, 300 rpm agitation) with capture antibody-coupled magnetic beads. Following three washes in a Bio-Plex Pro wash station, samples were incubated for 30 minutes in the dark (room temperature, 300 rpm agitation) with biotinylated detection antibody. Each captured analyte was detected by the addition of streptavidin-phycoerythrin and quantified using a BioPlex array reader. Analyte concentrations were calculated with Bio-Plex Manager software using a standard curve derived from the recombinant standard provided with the assays.

Cytokine Heat-Maps of DILI Subjects

Figure 3:
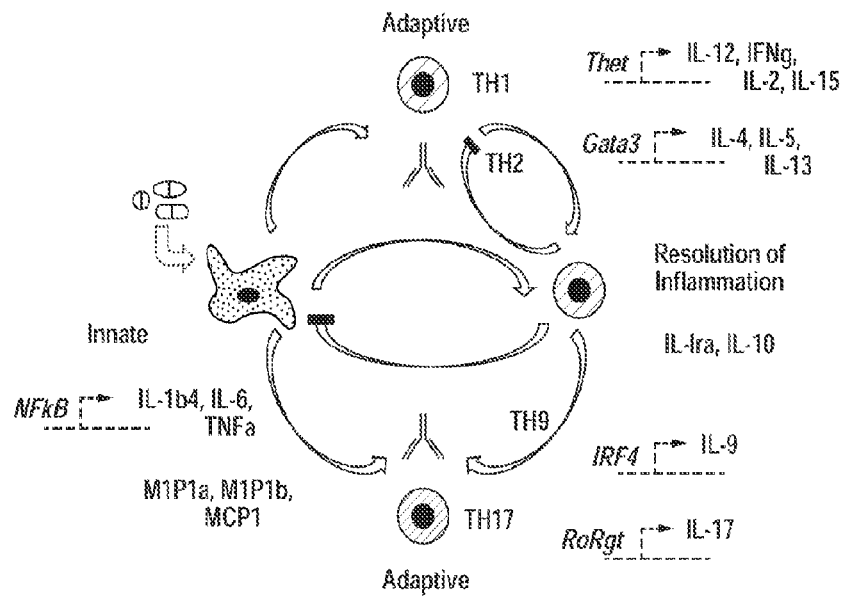
FIG. 3 illustrates a simplified model of immune responses.

To generate the cytokine heat-maps that were used to establish and compare immune response patterns among DILI subjects, cytokines were grouped, based on the major known transcription factors that originally trigger their expression and the immune processes to which they primarily relate, as follows: cytokines associated with innate immunity (NFκB-dependent): IL-1β, IL-6, TNFα; cytokines associated with adaptive cellular immunity (T-bet or RoRγt-dependent): IL-12p70, IFNγ, IL-2, IL-15, IL-17; cytokines associated with adaptive humoral immunity (Gata3 or IRF-4-dependent): IL-4, IL-5, IL-13, IL-9; and cytokines associated with immuno-suppression/resolution of inflammation: IL-1ra, IL-10 (29-33) as shown in FIG. 3. FIG. 3 illustrates a simplified model of immune responses. As shown in FIG. 3, immune stimuli trigger NFκB nuclear translocation and early/innate cytokine production (IL-1β, IL-6, TNF-α) by damaged tissue. If this early inflammatory state persists, it will activate adaptive immune processes favoring either cellular (T-bet-dependent/TH1-type: IL-12p70, IFNγ, IL-2, IL-15) or humoral (Gata3-dependent/TH2-type: IL-4, IL-5, IL-13) responses. This inflammatory state may ultimately resolve itself by triggering anti-inflammatory processes (IL-10, IL-1ra). In the event of an unresolved inflammatory state, innate and anti-inflammatory processes synergize to evolve into RoRγt-dependent/TH17-type: IL-17 or IRF4-dependent TH9-type IL-9 adaptive immunity.

Normal ranges for serum concentrations of immune analytes were based on measurements obtained from the 40 healthy controls and recorded as mean±1 standard deviation (SD). Concentrations in sera of DILI subjects 1 SD higher or lower than the means of healthy subjects were defined as abnormal. Four main immune profiles were identified, based on common recurrent patterns of abnormal cytokine expression among the DILI cohort at onset: 1) "mixed immune DILI" for those profiles in which at least 1 innate and 1 or more adaptive cellular and humoral cytokine concentrations were higher than normal; 2) "innate immune DILL" for profiles in which 1 or more innate cytokine concentrations were higher than normal and no adaptive cytokine were higher than normal; 3) "adaptive immune DILI" for profiles in which 1 or more adaptive cellular or humoral cytokine concentrations were higher than normal; and 4) "non-immune DILI" for profiles with only one (or none) serum abnormal cytokine concentrations Immune profiles that did not match any of the criteria described above were labeled as "uncategorized DILI."

Statistical Methods

Descriptive statistics, including means and standard deviations, or counts and percentages were calculated. For data measured on the interval scale, the Student's t-test or analysis of variance (ANOVA) was used. If the data were not normally distributed, the Wilcoxon rank sum test or the Kruskal-Wallis test was employed. The paired t-test or Wilcoxon signed rank test was used for comparing baseline values and the values at six months. For nominal data, the chi-square or Fisher's exact test was employed. Spearman's correlations were used to test for linear relationships between the variables measured on the interval scale. Unless specified otherwise, a two-tailed p-value of less than 0.05 was considered statistically significant. SAS® version 9.2 was used for all analyses.

The following modeling process was used to select variables among 27 immune analytes and 2 clinical lab test results (serum albumin or total bilirubin) for prediction of early death (within 6 month of DILI onset). Due to sample size and relatively large number of variables, the goal was to find a stable model (34) with small numbers of variables that are highly predictive of early death. In the first step, univariate analyses were carried out to compare those died within 6 months of DILI onset vs. those who survived by using the Wilcoxon rank sum test. To be highly selective, only those variables that were statistically significant at p<0.01 level were considered in the second step. It was expected that the immune analytes within each of the following three groups are likely to be correlated: cytokines, chemokines and growth factors. Thus in the second step, we examined the pairwise correlations within each group. We started out with the immune analyte that had the highest association with early death (lowest p-value). Only immune analytes within the group that were not significantly correlated with this immune analyte were retained for further consideration. If the pairwise correlations of the remaining immune analytes were significant, then we excluded the immune analyte with the lower association with early death from the pair. In the third step, we excluded immune analytes within the group that were poorly modulated based on heat-maps profiles of expressions. As a final step, we obtained the final set of the variables by examining the pairwise correlations among the remaining immune analytes and the clinical lab values. If the pairwise correlations were significant, then we excluded the variable with the lower association with early death from the pair.

Once the final set of variables was selected, the area under curve (AUC) was estimated for each variable to evaluate its potential prognostic and diagnostic value. Logistic regression model with all of these variables was fit to estimate the AUC based on the fitted model with linear combination of the variables as a predictor. The linear combination of these variables may not be the best predictor for early death because the values of the immune analytes can tend to be skewed. Thus, the following binary variables were created as predictors. The immune analytes were dichotomized at observed median values and the clinical lab values were dichotomized based on established clinical cutpoints. Two summary binary variables were created, one based on binary immune analytes only and the other based on both the binary immune analytes as well as clinical lab data. The binary variable based on both immune analytes and clinical lab data should have the highest predictability for early death. This binary variable has a value of 1 if values of the variables (immune analytes and clinical lab values) all fall in the binary category that was predictive of early death based on direction of association, and a value of 0 otherwise. The predictability of this binary variable for early death was evaluated by positive predictive value (PPV), negative predictive value (NPV) as well as accuracy (percent of correct prediction). Sensitivity and specificity were estimated as well for comparison.

Results

Characteristics of Study Cohorts

Figure 4:
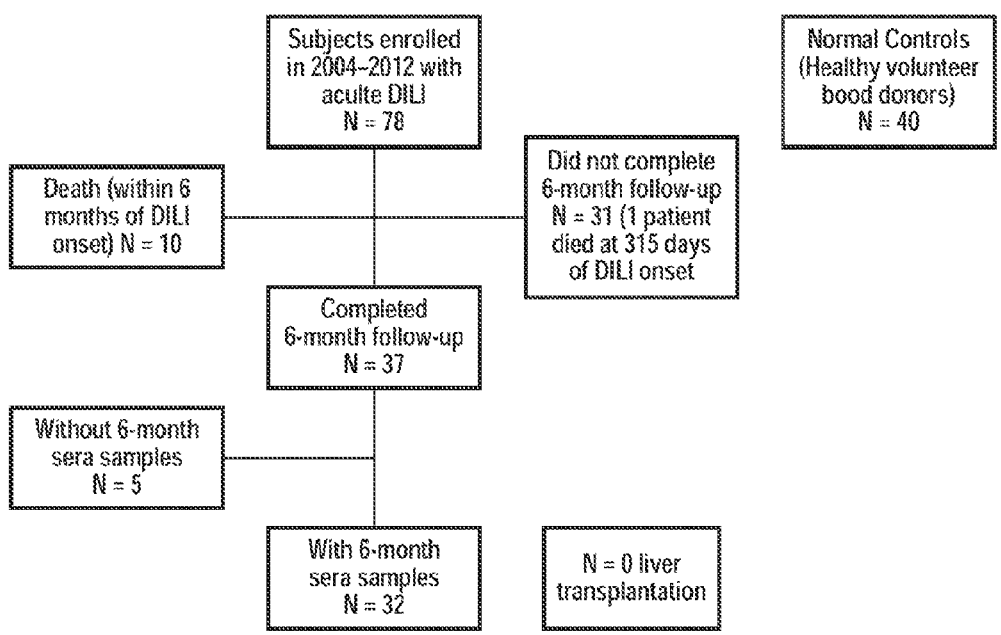
FIG. 4 shows a flow diagram of the illustrating the cohorts for a particular study.

As already described, a total of 78 DILI and 40 healthy subjects were included in the study (27) as illustrated FIG. 4. FIG. 4 graphically illustrates that sera from 78 DILI subjects and 40 healthy controls (volunteer blood donors) were analyzed in the study. Among those patients with acute DILI, 10 died within 6 months of DILI onset and 37 returned for a 6-month follow-up visit, among whom serum samples were obtained from 32.

As noted above, thirty-seven subjects completed 6 months follow-up among whom follow-up sera samples were obtained for 32 DILI patients (due to various reasons, 5 patients did not provide serum samples at 6 months). Ten subjects (12.8%) are known to have died within 6 months of DILI onset, whereas one died of a non-DILI cause 315 days following DILI onset. None underwent liver transplantation. Evaluation of the reasons for the surviving 31 subjects who did not complete 6 month follow-up visits indicated that majority of them were due to scheduling conflicts with work or traveling distances that were too great.

Detailed demographic and liver chemistries information of all subjects included in the study are presented in Table 2, below.

TABLE 2

Selected demographic, clinical, and laboratory features of subjects studied.

|  | DILI onset (n = 78) | 6-month follow-up (n = 32) | Healthy controls (n = 40) |
| --- | --- | --- | --- |
| Age, mean ± SD (y) | 48 ± 17.9 | 51 ± 14.2 | 49.2 ± 13.1 |
| Female (%) | 55 | 55 | 28 |
| Self-reported race (%) | | | |
| White | 73 | 73 | 95 |
| Black | 10 | 10 | 5 |
| Other | 16 | 15 | 0 |
| Unknown | 1 | 0 | 0 |
| Body mass index, mean ± SD (kg/m2) | 27.1 ± 6.5 | | 30.5 ± 6.9 |
| Alcohol use (%) | 40 | | |
| Preexisting liver disease (%) | 8 | | |
| Prior drug allergies (%) | 53 | | |
| Diabetes mellitus (%) | 32 | | |
| Absolute eosinophils/µL (mean ± SD) | 173 ± 235 | | |
| Liver biochemistries, mean ± SD | | | |
| ALT (U/L) | 1065 ± 1382 | 55 ± 131 | 17 ± 5 |
| AST (U/L) | 1003 ± 1249 | 38 ± 47 | 24 ± 5 |
| Alkaline phosphatase (U/L) | 336 ± 465 | 89 ± 33 | 63 ± 14 |
| Total bilirubin (mg/dL) | 8.1 ± 7.4 | 0.9 ± 0.7 | 0.6 ± 0.2 |
| INR | 1.8 ± 1.2 | 1.1 ± 0.4 | |

Abbreviations:
DILI, Drug-induced liver injury;
SD, standard deviation;
ALT, alanine aminotransferase;
AST, aspartate aminotransferase;
INR, international normalized ratio.

Briefly, the mean age of the DILI cohort was 48 (±17.9) years old. Gender distribution was 55% women and the majority of patients (73%) were Caucasian. Six of the 78 (8%) DILI subjects had preexisting liver disease; 25 (32%) presented with underlying diabetes mellitus. As shown in Table 3, 59%, 22%, 15% and 4% of DILI subjects, respectively, presented with hepatocellular, cholestatic, mixed or unknown pattern of liver injury. These percentages are similar to those of the entire DILI cohort (10).

TABLE 3

Selected DILI characteristics and outcomes among subjects studied [n = 78].

| Pattern of liver injury (%) | |
| --- | --- |
| Hepatocellular | 59 |
| Cholestatic | 22 |
| Mixed | 15 |
| Unknown | 4 |
| Severity of liver injury (%) | |
| Mild | 11 |
| Moderate | 49 |
| Severe/fatal | 26 |
| Unknown | 14 |
| Liver-related mortality (%) | 6 |
| Chronic DILI (%) | 5 |

Longitudinal Analysis: Immune Analytes and the Course of DILI

Experimental models of DILI and retrospective clinical studies (15-18, 20-24) have posited immune activation mechanisms associated with acute liver injury. In order to characterize immune components associated with DILI regardless of the pattern and severity of injuries, serum levels of immune analytes were compared among DILI onset (n=78), 6-month follow-up (n=32) and healthy controls (n=40). The three groups displayed a high degree of heterogeneity. For 26 of the 27 immune analytes, the results were not normally distributed.

A Wilcoxon rank-sum test was performed to assess which cytokines, chemokines or growth factors, were altered in DILI as illustrated in Table 3 (shown below). Distributions of serum levels of 10 immune analytes significantly differed among healthy controls, DILI at onset and DILI at 6-month follow up. These 10 were IL-4, IL-5, IL-7, IL-8, IL-9, IFN-γ, eotaxin, RANTES, PDGF-bb, and MCP-1. In addition, serum levels of 4 immune analytes were differently distributed between control and DILI at onset (IL-6, IL-13, IP-10, FGF basic), and 4 (IL-2, IL-15, VEGF, MIP-1β) were differently distributed between control and DILI at 6-month follow-up (Table 4). For those subjects with 6-month follow-up samples (n=32), the differences between the baseline and follow-up samples were examined. Significant changes were observed for 8 immune analytes (IL-5, IL-8, IP-10, IFNγ, FGF basic, MIP-1β, GM-CSF and VEGF) (Table 4). Overall, among the 27 immune analytes investigated, 19 showed significant differences among healthy controls and DILI at onset and/or at 6-month follow-up.

TABLE 4

Summary of immune analyte serum levels at DILI onset, 6-month follow-up, and in controls. All results are pg/mL.

| | DILI onset | | | 6-month follow-up | | | Control | | |
| --- | --- | --- | --- | --- | --- | --- | --- | --- | --- |
| | Median | Min. | Max. | Median | Min. | Max. | Median | Min. | Max. |
| Cytokines associated with Innate Immunity | | | | | | | | | |
| IL-1β | 0.9 | 0.0 | 48.2 | 1.5 | 0.0 | 18.8 | 1.2 | 0.0 | 4.8 |
| IL-6[b] | 11.0 | 0.4 | 970.5 | 7.7 | 0.1 | 47.4 | 5.1 | 2.2 | 45.7 |
| TNFα | 17.1 | 0.0 | 326.5 | 27.0 | 0.0 | 298.5 | 22.7 | 0.0 | 116.6 |
| Adaptive Cellular Immunity | | | | | | | | | |
| IL-12 | 15.7 | 0.0 | 2186 | 24.9 | 2.8 | 636.3 | 16.0 | 5.7 | 294.8 |
| IFNγ[a,d] | 41.6 | 0.0 | 285.1 | 51.5 | 5.7 | 626.5 | 58.5 | 11.5 | 413.0 |

TABLE 4-continued

Summary of immune analyte serum levels at DILI onset, 6-month follow-up, and in controls.
All results are pg/mL.

|  | DILI onset | | | 6-month follow-up | | | Control | | |
|---|---|---|---|---|---|---|---|---|---|
|  | Median | Min. | Max. | Median | Min. | Max. | Median | Min. | Max. |
| IL-2[c] | 2.4 | 0.0 | 660.5 | 0.0 | 0.0 | 93.2 | 4.2 | 0.0 | 148.8 |
| IL-15[c] | 2.4 | 0.0 | 28.9 | 0.0 | 0.0 | 19.7 | 3.6 | 0.0 | 94.2 |
| IL-17 | 45.2 | 0.0 | 156.7 | 53.3 | 0.0 | 153.4 | 52.7 | 23.5 | 118.3 |
| Adaptive Humoral Immunity | | | | | | | | | |
| IL-4[a] | 5.6 | 0.0 | 12.7 | 5.6 | 1.0 | 10.2 | 9.8 | 1.2 | 12.9 |
| IL-5[a,d] | 3.0 | 0.0 | 68.4 | 4.2 | 0.2 | 69.1 | 3.8 | 1.5 | 27.6 |
| IL-13[b] | 2.7 | 0.0 | 130.1 | 4.0 | 0.0 | 95.7 | 3.24 | 0.2 | 95.0 |
| IL-9[a] | 13.6 | 0.0 | 2194.0 | 11.2 | 0.0 | 795.7 | 20.0 | 11.2 | 99.1 |
| Immuno-suppression/ resolution | | | | | | | | | |
| IL-1ra | 137.7 | 4.7 | 1406 | 126.6 | 41.1 | 663.3 | 145.4 | 18.8 | 284.4 |
| IL-10 | 4.3 | 0.0 | 2494 | 2.7 | 0.0 | 373.3 | 3.0 | 0.0 | 287.5 |
| Chemokines | | | | | | | | | |
| Eotaxin[a] | 41.2 | 0.0 | 195.3 | 44.8 | 0.0 | 365.7 | 106.4 | 3.3 | 808.0 |
| IL-8[a,d] | 69.1 | 7.4 | 4636.0 | 28.6 | 4.1 | 141.5 | 28.5 | 8.6 | 82.0 |
| IP-10[b,d] | 1378.5 | 71.9 | 48050 | 749.9 | 177.7 | 7337.5 | 625.8 | 20.1 | 1663 |
| MCP-1[a] | 22.64 | 0.0 | 399.3 | 23.8 | 0.0 | 66.2 | 42.4 | 12.1 | 147.5 |
| MIP-1α | 3.4 | 0.0 | 80.1 | 3.9 | 0.0 | 27.6 | 3.5 | 1.7 | 30.3 |
| MIP-β[c,d] | 84.1 | 15.6 | 473.6 | 72.5 | 15.2 | 223.4 | 95.7 | 5.3 | 190.2 |
| RANTES[a] | 2529.0 | 190.0 | 65180 | 2615.2 | 441.4 | 43545 | 7227.4 | 14.5 | 65180 |
| Growth Factors | | | | | | | | | |
| IL-7[a] | 7.0 | 0.0 | 165.0 | 10.4 | 0.7 | 103.2 | 9.4 | 5.0 | 104.1 |
| FGF b[b,d] | 10.9 | 0.0 | 67.9 | 21.5 | 0.0 | 164.5 | 16.6 | 0.0 | 108.2 |
| G-CSF | 19.0 | 5.7 | 425.1 | 17.8 | 2.7 | 118.7 | 21.7 | 9.3 | 61.4 |
| GM-CSF[d] | 0.0 | 0.0 | 86.7 | 0.0 | 0.0 | 23.6 | 0.0 | 0.0 | 413.4 |
| PDGF-bb[a] | 4207.0 | 65.3 | 28757 | 3595.1 | 697.2 | 23350 | 12037 | 12.1 | 34353 |
| VEGF[c,d] | 62.4 | 0.0 | 620.8 | 42.3 | 3.1 | 136.6 | 84.4 | 19.0 | 411.6 |

[a] Comparisons of all distributions to control samples are statistically significant (p < 0.05) by Wilcoxon rank sum test
[b] Comparisons of the onset distributions to control samples are statistically significant (p < 0.05) by Wilcoxon rank sum test
[c] Comparisons of the 6-month follow-up distributions to control samples are statistically significant (p < 0.05) by Wilcoxon rank sum test
[d] Comparisons of the difference between the onset distributions and 6-month follow-up distributions are statistically significant (p < 0.05) by paired t-test or Wilcoxon signed rank test Comparative Analysis of Immune Analyte Pattern(s) of DILI Subjects To provide a framework better to understand the heterogeneity observed in control, DILI onset, and DILI 6-month groups, immune profiles of individual DILI subjects were assessed and compared. These immune profiles were established based on cytokine serum levels and from consideration of known immunological principles. While the function and origin of individual immune analytes can be determined, cytokines actually function in networks (synergy, antagonism). For instance, in a simplified model of immune processes (FIG. 3), an immune stimulus (e.g. cell damage caused by a drug or other chemical) triggers NFκB nuclear translocation and early/innate cytokine production (IL-1β, IL-6, TNF-α) by damaged tissue. If this early inflammatory state persists, it will activate adaptive immune processes favoring either cellular (T-bet-dependent/TH1-type: IL-12p70, IFNγ, IL-2, IL-15; RoRγt-dependent/TH17-type: IL-17) or humoral (Gata3-dependent/TH2-type: IL-4, IL-5, IL-13; IRF4-dependent/TH9-type: IL-9) responses (29, 30, 33). Usually, immune responses will ultimately resolve themselves by triggering anti-inflammatory processes (IL-10, IL-1ra) (32).

To Serum cytokine profiles for DILI subjects were determined by comparing each immune analyte to values of 'normal' healthy controls. Cytokine measurements more than 1 SD higher or lower than the healthy control average were considered 'abnormal'. Using this approach, 4 distinct immune profiles emerged among DILI subjects at the onset of the disease (n=78) as illustrated in FIG. 5. Nineteen subjects (24.3%) displayed an "innate immunity" pattern with one or more early/innate cytokines higher than normal. Twenty-one patients (26.9%) showed an "adaptive immunity" immune pattern with at least one adaptive cytokine higher than normal. Four subjects had a "mixed immune DILI" pattern (both early and innate cytokines higher than normal), and 8 a "non-immune DILI" profile (1 or fewer abnormal cytokine levels). Finally, 26 subjects (33.3%) were uncategorized (2 or more abnormal cytokines levels). Of note, among the 21 subjects with an "adaptive immunity" cytokine profile, the classical TH1 and TH2 adaptive responses were rare. Rather at DILI onset, TH17 (15.4% of the total DILI cohort) and TH9 (6.4% of the total DILI cohort) increases predominated in this group as shown in FIG. 5.

Moreover, FIG. 5 illustrates individual cytokine concentrations in sera obtained close to (within 14 days of) DILI onset that were recorded for each patient and compared with healthy "normal" means±SD values. Abnormal serum cytokine concentrations at DILI onset were defined as values that were higher (red) or lower (blue) than those of the means for normal controls. The profiles of DILI subjects at onset were defined based on observed similarities of patterns and upon knowledge of the physiologic roles of the analytes.

Using a similar methodology to compare the 32 DILI subjects for whom 6-month follow-up samples and data were available, 12 (37.5%) exhibited normal or lower than normal serum cytokine levels and 17 (53.1%) DILI subjects showed higher than normal serum levels of adaptive cytokines as shown in FIG. 6. Among the cohort of 32, overexpressed adaptive cytokines were predominantly TH1 (6/32) or cellular/humoral hybrid (6/32). Only a few subjects displayed TH17 (4/32) or TH9 profiles (1/32) as shown in FIG. 6.

In particular, FIG. 6 shows profiles of cytokines in sera of DILI subjects at 6-month follow-up. Individual cytokine concentrations in 6-month follow-up sera were recorded for each patient and compared with healthy "normal" means±SD values. Abnormal serum cytokine concentrations at 6-mo follow-up were defined as measurements SD higher (red) or lower (blue) than those of the means for normal controls. The profiles of DILI subjects at 6 month follow up were defined based on observed similarities of patterns and upon knowledge of the physiologic roles of the analytes.

Validation of Cytokine Profiling Methodology

To test the accuracy of innate vs. adaptive cytokine grouping in the DILI onset cohort, and therefore the validity of our cytokine profiling methodology, individual chemokine expression profiles were analyzed. Heat-maps were created for three NFκB-dependent (MIP1α, MIP1β, MCP-1) (35, 36) and one IRF3-dependent (IP10) chemokines (37), and compared to the cytokine profiles described above.

As already described, chemokine measurements more than 1 SD higher or lower than the healthy control average were considered 'abnormal' as shown in FIG. 7. Among the 19 "innate immunity" patients, 14 (73.6%) also showed one or more NFκB-dependent chemokine higher than normal while only 4 (21%) had abnormally elevated IP10 expression. Performing the same comparisons with the 21 "adaptive immunity" patients, only 5 (23.8%) had one or more higher than normal NFκB-dependent chemokine, but all also showed higher than normal innate cytokine expression as shown in FIG. 7. Finally, 5/26 (19.2%) uncategorized DILI patients showed higher than normal expression of MIP1α, MIP1β or MCP-1 similar to what was observed with hyperimmune DILI patients.

In particular, FIG. 7 shows profiles of chemokines in sera of DILI subjects at DILI onset. Individual chemokine concentrations in sera were recorded for each patient at DILI onset and compared with healthy "normal" means±SD values. Abnormal serum chemokine concentrations at onset were defined as measurements higher (red) or lower (blue) than those of the means for normal healthy controls. Expression of 3 NFκB-dependent (MIP1α, MIP1β, MCP-1) and an IRF3-dependent (IP10) chemokines were compared to previously established cytokine profiles.

Immune Analytes and Clinical Features of DILI

Correlations among clinical features and cytokine levels were explored. Several cytokines, chemokines and growth factors were found to be significantly associated with hyperbilirubinemia (serum total bilirubin>1.2 mg/dL) and self-reported jaundice. See Table 5, below. As expected, there was a significant association between hyperbilirubinemia and self-reported jaundice (median serum total bilirubin for self-reported jaundice=8.7 mg/dL, median for subjects not reporting jaundice=0.9 mg/dL, p<0.001). Those with hyperbilirubinemia or self-reported jaundice had mean serum ALT and AST levels that were not significantly different from those of other DILI subjects. The median values for nearly all of the immune analytes were higher for subjects with hyperbilirubinemia or self-reported jaundice compared to those without. No significant association was evident for the following clinical features and any of the cytokines measured: gender, age, pattern of DILI, severity of DILI, serum ALT at onset, peak serum ALT, serum AP at onset, peak serum AP, R value (i.e.: [serum ALT/ULN ALT] divided by [serum AP/ULN AP]), BMI, absolute eosinophil count, history of infectious disease, history of psychiatric disease, history of heart disease, history of systemic arterial hypertension, history of renal disease, history of pulmonary disease, history of GI disease, history of malignant disease (data not shown). In addition, there were no significant associations among the concentrations or profiles of immune analytes and the major therapeutic classes of the causative drugs (anti-infectious agents, anti-convulsants, anti-hypertensive agents, lipid lowering agents, immuno-suppressants and, anti-cancer chemotherapeutic agents).

TABLE 5

Serum levels at DILI onset of immune analytes significantly associated with an elevation of serum total bilirubin
All results are pg/mL.

|  | Serum Total Bilirubin >1.2 mg/dL | | | Serum Total Bilirubin 0-1.2 mg/dL | | | p value* |
| --- | --- | --- | --- | --- | --- | --- | --- |
|  | Median | Min. | Max. | Median | Min. | Max. |  |
| IL-1β | 1.0 | 0.0 | 48.2 | 0.6 | 0.0 | 2.5 | 0.035 |
| IL-1ra | 145.6 | 29.1 | 719.6 | 81.6 | 4.7 | 1406 | 0.007 |
| IL-5 | 3.1 | 0.5 | 68.4 | 2.1 | 0.0 | 6.5 | 0.0156 |
| IL-7 | 8.0 | 1.4 | 165.0 | 3.7 | 0.0 | 13.8 | 0.0131 |
| IL-8 | 82.7 | 15.6 | 4636 | 42.7 | 7.4 | 463.1 | 0.0043 |
| IP-10 | 2163.6 | 222.6 | 48050 | 835.2 | 71.9 | 39266 | 0.0124 |
| MIP-1α | 3.6 | 0.0 | 80.1 | 1.4 | 0.0 | 12.0 | 0.0184 |
| MIP-1β | 99.5 | 19.3 | 473.8 | 54.7 | 15.6 | 158.4 | 0.0011 |
| PDGF-bb | 4819 | 65.3 | 28757 | 1772.5 | 130.9 | 15951 | 0.0101 |

*Comparisons of distributions are statistically significant (p < 0.05) by Wilcoxon rank sum test Immune Analytes and DILI Outcomes Results of immune analyte profiles and clinical lab tests of serum albumin and total bilirubin at baseline were examined for patterns predictive of early death within 6 months of DILI onset. The modeling process selected the following five variables to be used for prediction: four immune analysts (IL-9, IL-17, PDGF-bb and RANTES) and serum albumin Step 1 of the modeling process showed that 7 cytokines (TNFα, IL-12, IL-17, IL-4, IL-5, IL-13, IL-9), 2 chemokines (MIP-1β, Rantes), 2 growth factors (FGFb, PDGF-bb) and albumin were significantly (at level of 0.01) associated with death with 6 months of DILI onset as illustrated in Table 6 based on univariate analyses. Four cytokines (TNFα, IL-12, IL-4, IL-5) and one growth factor (FGFb) were excluded in step 2 due to their significant correlations with the highest ranked (based on p-values) cytokine IL-17 and highest ranked growth factor PDGF-bb. Cytokine IL-13 was excluded in step 3 because it was poorly modulated based on the heat map of cytokine expression profile (e.g., See Table 5). Chemokine MIP-1β was excluded in the final step due to its significant correlation with growth factor PDGF-bb.

TABLE 6

Serum levels at DILI onset of immune analytes significantly associated
with death within 6 months of DILI onset.
Analyte results are pg/mL.

|  | Died [n = 10] | | | Survived [n = 68] | | | |
|---|---|---|---|---|---|---|---|
|  | Median | Min. | Max. | Median | Min. | Max. | p value* |
| Cytokines | | | | | | | |
| TNFα | 0.5 | 0.0 | 30.9 | 20.1 | 0.0 | 326.5 | 0.001 |
| IL-12 | 3.1 | 0.0 | 27.4 | 16.7 | 0.0 | 2185.6 | <0.001 |
| IL-17 | 8.6 | 0.0 | 156.7 | 47.4 | 0.0 | 139.1 | <0.001 |
| IL-4 | 2.3 | 0.0 | 5.8 | 5.8 | 0.5 | 12.7 | <0.001 |
| IL-5 | 1.1 | 0.0 | 4.9 | 3.0 | 0.0 | 68.4 | 0.006 |
| IL-13 | 0.7 | 0.0 | 4.0 | 2.8 | 0.0 | 130.1 | <0.001 |
| IL-9 | 6.7 | 0.0 | 17.1 | 15.5 | 0.0 | 2194.2 | 0.003 |
| Chemokines | | | | | | | |
| MIP-1β | 55.1 | 19.3 | 133.1 | 92.4 | 15.6 | 473.8 | 0.006 |
| RANTES | 1412.8 | 190.0 | 2301.2 | 2740.6.8 | 761.4 | 65180 | <0.001 |
| Growth Factors | | | | | | | |
| FGFb | 0.0 | 0.0 | 15.7 | 13.5 | 0.0 | 67.9 | 0.003 |
| PDGF-bb | 487.0 | 65.3 | 7313.1 | 4719.4 | 130.9 | 28757 | <0.001 |
| Clinical Lab | | | | | | | |
| Albumin | 2.3 | 1.8 | 2.8 | 3.1 | 1.8 | 4.9 | 0.001 |

*Comparisons of distributions are statistically significant (p ≤ 0.01) by Wilcoxon rank sum test Low values of immune analytes and low value of serum albumin were predictive of early death with estimated AUCs (95% CI) of 0.79 (0.65, 0.93) for IL-9, 0.86 (0.67, 1.0) for IL-17, 0.84 (0.68, 1.0) for PDGF-bb, 0.90 (0.81-0.98) for Rantes, and 0.83 (0.73, 0.94) for serum albumin. The AUC (95% CI) of the linear combination of these variables based on the logistic regression model was 0.98 (0.95, 1.0). Because the values of the immune analytes were highly skewed, binary variables were created to combine and to summarize the information from these variables. The observed median values of the four immune analytes and the known cutpoint of 2.8 g/dL (used in the Child-Turcotte-Pugh scoring system for identifying subjects with class C liver disease) for albumin were used to dichotomize the continuous variables into binary variables. Subjects in the DILI cohort with a baseline value of serum albumin greater than 2.8 g/dL all survived with 100% NPV, whereas all of those who died within 6 months of DILI onset had values below this cutoff with 100% sensitivity as illustrated in Table 7. The binary variable based on the final four immune analytes (11-9, IL-17, PDGF-bb and RANTES) had estimated PPV, NPV and accuracy of 67%, 97% and 92%, respectively, if values of four immune analytes were all below the observed medians. Combination of the four binary immune analytes and binary serum albumin provided optimal differentiation between those who died of acute DILI or survived for at least six months (and usually recovered completely). Using this benchmark, 67 (97% NPV) out of 69 subjects with IL-9>13.6, IL-17>45.2, PDGF-bb>4207, RANTES>2529 or albumin>2.8 g/dL survived the acute DILI event at 6 months, whereas 7 (88% PPV) out of 8 subjects with IL-9<13.6, IL-17<45.2, PDGF-bb<4207, RANTES<2529 and albumin≤2.8 g/dL died within 6 months of DILI onset (Table 7). The overall accuracy of prediction is 74/77=96% (95% CI, 92%-100%). Baseline MELD scores were also explored for predictability for early death. As shown in Table 8, MELD scores (38) also predicted with some accuracy, albeit not as well as for the combined binary variable of 4 immune analytes and albumin. Unfortunately, all data necessary for the calculation of MELD scores were available for only 34 of the 78 subjects studied, including 6 of the 10 who died within six months. The values often missing were the serum creatinine and INR.

TABLE 7

Binary Variables predictive of death within 6 months of DILI onset.

|  | Acute death (<6 months) | Survival At 6-months | Sensitivity (95% CI) | Specificity (95% CI) | Positive predictive value (98% CI) | Negative pedictive value (95% CI) | Accuracy (95% CI) |
|---|---|---|---|---|---|---|---|
| Serum albumin (N = 74)* | | | | | | | |
| ≤2.8 g/dL | 9 | 26 | 100% | 60% | 26% | 100% | 65% (54%, 76%) |
| >2.8 g/dL | 0 | 39 | (N/A) | (48%, 725) | (11%, 40%) | (N/A) | |
| Four immune analytes (IL-9, IL_17, PDGF-bb RANTES) (N = 78) | | | | | | | |
| All immune analytes below medians** | 8 | 4 | | | | | |

TABLE 7-continued

Binary Variables predictive of death within 6 months of DILI onset.

| | Acute death (<6 months) | Survival At 6-months | Sensitivity (95% CI) | Specificity (95% CI) | Positive predictive value (98% CI) | Negative pedictive value (95% CI) | Accuracy (95% CI) |
|---|---|---|---|---|---|---|---|
| At least one above median Four immune analytes (IL-9, IL_17, PDGF-bb RANTES) and serum albumin (N = 77)*** | 2 | 64 | 80% (55%, 100%) | 94% (89%, 100%) | 67% (40%, 675) | 97% (93%, 100%) | 92% (86%, 98%) |
| All immune analytes below medians** and albumin ≤2.8 g/dL | 7 | 1 | | | | | |
| At least one immune analyte above median or albumin >2.8 g/dL | 2 | 67 | 78% (51%, 100%) | 99% (96%, 100%) | 88% (65%, 100%) | 97% (93%, 100%) | 96% (92%, 100%) |

*Four subjects were excluded due to missing values of serum albumin at DILI onset
**IL-9 <13.6, IL_17 <45.2, PDGF-bb <4207, RANTES <2529 where the numbers are observed medians for 78 subjects.
***One subject was excluded whose category could not be determined due to missing serum albumin result and values of all four immune analytes were below the medians.

TABLE 8

Deaths actual vs. predicted, using MELD scores at baseline for DILI subjects (n = 34).

| MELD Score | n | Actual Deaths | Predicted Deaths |
|---|---|---|---|
| >40 | 2 | 0/2 = 0% | 71.3% |
| 30-39 | 5 | 4/5 = 80% | 52.6% |
| 20-29 | 10 | 2/10 = 20% | 19.6% |
| 10-19 | 16 | 0/16 = 0% | 6.0% |
| <10 | 1 | 0/1 = 0% | 1.9% |

The study discussed above provides at least the following main findings: 1) profiles of serum immune analytes are altered in acute DILI; 2) such profiles may be classified into different types; 3) profiles are not specific to or correlated with the underlying drug causes of DILI, with the pattern of DILI, whether hepatocellular, cholestatic, or "mixed", nor with the R value at baseline or at later time points; and 4) low values of serum albumin and a summary variable of only four immune analytes at DILI onset (IL-17, IL-9, PDGF-bb and RANTES) are predictive, in accordance with certain embodiments of the present invention, of who will survive and who will not survive for 6 months after an acute DILI event. Such, embodiments according t the present invention, therefore, beneficially provide the ability to predict early in the course of acute DILI those subjects who are likely to survive or not survive.

With respect to advancing the understanding of pathogenesis of DILI, differing immune response patterns are suggested from analysis of cytokine profiling of DILI subjects that provide valuable new insights. It is increasingly clear that DILI is often due to an exuberant immunological response to a drug (or drug metabolite), usually bound to host proteins. For example, serum albumin has been implicated as a frequent "schlepper" of drug-derived haptens, and these complexes have called forth immune responses that lead to liver injury (7, 39-41). Such responses, directed chiefly at hepatocytes or at bile ductular cells, may also attack other organs and tissues, particularly the skin, the kidneys or the bone marrow (42). The current paradigm for immunological characterization of DILI [autoimmune-like or immuno-allergic] is based on clinico-pathological manifestation of the disease, presence of autoantibodies (adaptive immunity), eosinophila (innate immunity) and/or skin rash (7, 43). Autoimmune type DILI tends to have a delayed onset and tends to evolve slowly on rechallenge (44). Skin rashes, a mark of immuno-allergic-like DILI, can be triggered by either innate immune or adaptive immune components (e.g. DRESS syndrome, systemic lupus erythematosus) (45, 46). Taken together, the prototypical autoimmune-like or immuno-allergic categories of DILI show overlap, which is in keeping with clinical experience, with data in the US DILIN database, and with clinical reports from DILIN [(47-49) and Ghabril et al, Russo et al, unpublished observations]. The cytokine and chemokine profiling analyses described above highlight the innate immune component in DILI (19/78 subjects), and illustrate a distinct adaptive immune component at DILI onset that is mostly cellular (21/78 subjects). Interestingly, abnormal classical or canonical TH1 and TH2 adaptive cytokine expressions were rare in the DILI cohort investigated (4/78 subjects), whereas exuberant TH17 and TH9 innate immune responses were more prevalent (17/78 subjects).

Recent studies investigating individual drugs have provided evidence for a major contribution of the TH17 pathway in DILI (19, 50). While we found abnormal IL-17 serum concentrations to be a hallmark of "adaptive immunity DILI", the mechanisms by which the TH17 pathway contribute to the pathology remain to be elucidated. Auto reactive TH17 cells, which have been implicated in chronic auto-immune conditions such as multiple sclerosis and colitis, are predominantly driven by dysregulated TH17 pathways (51, 52). Further characterization of TH17 cells in "adaptive immunity DILI" with a particular emphasis on auto-reactivity may clarify whether IL-17 is linked to cellular autoimmunity. In rheumatoid arthritis, it has recently been shown that IL-17 can promote autoantibody production (53). Nonetheless, we found no correlation between abnormal TH17 production and the presence of autoantibodies at DILI onset. In numerous instances of chronic liver pathologies/injuries (alcoholic liver disease, nonalcoholic steatohepatitis, autoimmune liver disease) a TH17 component has been identified (50), suggesting that patients who display higher than normal serum IL-17 concentrations at DILI onset may be predisposed [or more likely] to have long lasting and unresolved liver injury.

A major clinical dilemma is to know which subjects with acute DILI are going to recover uneventfully (assuming that the offending drug is discontinued promptly) and which, despite drug discontinuation, are going to progress to liver failure and death within six months or need for liver transplantation. Certain embodiments of the present invention provides critical information to categorize subjects very early in the course of DILI.

In accordance with certain embodiments of the present invention, a single binary predictor is relatively easy to use requiring measurement of only serum albumin and four immune analytes (i.e., 11-9, IL-17, PDGF-bb and RANTES) early in the course of the disease. This particular binary predictor, according to certain embodiments of the present invention, exhibits a high accuracy in predicting death of acute DILI [Table 6]. Of particular importance is that two fundamentally different strategies employed to analyze immune analyte measurements i.e., a strategy based upon the known biological function and regulation of immune analytes and a statistical/mathematical strategy, based upon the results observed in these studies, converged to give two main findings: 1) IL-17 (and to a lesser extent IL-9) are key contributors to the pathology of DILI at onset (more precisely "adaptive immunity DILI"), and 2) low IL-17/IL-9 serum concentrations are associated with poor prognosis of DILI, or reciprocally, "adaptive immunity DILI" is associated with a good prognosis.

Many modifications and other embodiments of the invention set forth herein will come to mind to one skilled in the art to which these inventions pertain having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

CITED LITERATURE (Each of which is Hereby Incorporated by Reference)

1. Ostapowicz, G., R. J. Fontana, F. V. Schiodt, A. Larson, T. J. Davern, S. H. Han, T. M. McCashland, A. O. Shakil, J. E. Hay, L. Hynan, J. S. Crippin, A. T. Blei, G. Samuel, J. Reisch, and W. M. Lee. 2002. Results of a prospective study of acute liver failure at 17 tertiary care centers in the United States. Ann Intern Med 137:947-954.
2. Reuben, A., D. G. Koch, and W. M. Lee. 2010. Drug-induced acute liver failure: results of a U.S. multicenter, prospective study. Hepatology 52:2065-2076.
3. Bjornsson, E. 2010. Review article: drug-induced liver injury in clinical practice. Aliment Pharmacol Ther 32:3-13.
4. Navarro, V. J., and J. R. Senior. 2006. Drug-related hepatotoxicity. N Engl J Med 354:731-739.
5. Watkins, P. B., and L. B. Seeff. 2006. Drug-induced liver injury: summary of a single topic clinical research conference. Hepatology 43:618-631.
6. Abboud, G., and N. Kaplowitz. 2007. Drug-induced liver injury. Drug Saf 30:277-294.
7. Bonkovsky, H. L., S. I. Shedlofsky, D. P. Jones, and M. Russo. 2012. "Drug-induced liver injury". Chapter 25 in Boyer T D, Manns M P and Sanyal A (Eds), Zakin and Boyer's Hepatology—a textbook of liver disease, 6th edition, Saunder-Elsevier, Philadelphia, pp 417-461.
8. Chalasani, N., and E. Bjornsson. 2010. Risk factors for idiosyncratic drug-induced liver injury. Gastroenterology 138:2246-2259.
9. Au, J. S., V. J. Navarro, and S. Rossi. 2011. Review article: Drug-induced liver injury—its pathophysiology and evolving diagnostic tools. Aliment Pharmacol Ther 34:11-20.
10. Chalasani, N., R. J. Fontana, H. L. Bonkovsky, P. B. Watkins, T. Davern, J. Serrano, H. Yang, and J. Rochon. 2008. Causes, clinical features, and outcomes from a prospective study of drug-induced liver injury in the United States. Gastroenterology 135:1924-1934, 1934 e1921-1924.
11. Wai, C. T., B. H. Tan, C. L. Chan, D. S. Sutedja, Y. M. Lee, C. Khor, and S. G. Lim. 2007. Drug-induced liver injury at an Asian center: a prospective study. Liver Int 27:465-474.
12. Zimmerman, H. J. 1999. Hepatotoxicity: the adverse effects of drugs and other chemicals on the liver. 2nd edition, Lippincott Williams & Wilkins.
13. Sgro, C., F. Clinard, K. Ouazir, H. Chanay, C. Allard, C. Guilleminet, C. Lenoir, A. Lemoine, and P. Hilton. 2002. Incidence of drug-induced hepatic injuries: a French population-based study. Hepatology 36:451-455.
14. Shi, Q., H. Hong, J. Senior, and W. Tong. 2010. Biomarkers for drug-induced liver injury. Expert Rev Gastroenterol Hepatol 4:225-234.
15. Takayama, H., Y. Miyake, K. Nouso, F. Ikeda, H. Shiraha, A. Takaki, H. Kobashi, and K. Yamamoto. 2011. Serum levels of platelet-derived growth factor-BB and vascular endothelial growth factor as prognostic factors for patients with fulminant hepatic failure. J Gastroenterol Hepatol 26:116-121.
16. Pachkoria, K., M. I. Lucena, E. Crespo, F. Ruiz-Cabello, S. Lopez-Ortega, M. A. Fernandez, M. Romero-Gomez, A. Madrazo, J. A. Duran, A. M. de Dios, Y. Borraz, J. M. Navarro, and R. J. Andrade. 2008. Analysis of IL-10, IL-4 and TNF-alpha polymorphisms in drug-induced liver injury (DILI) and its outcome. J Hepatol 49:107-114.
17. Laverty, H. G., D. J. Antoine, C. Benson, M. Chaponda, D. Williams, and B. Kevin Park. 2010. The potential of cytokines as safety biomarkers for drug-induced liver injury. Eur J Clin Pharmacol 66:961-976.
18. Aithal, G. P., L. Ramsay, A. K. Daly, N. Sonchit, J. B. Leathart, G. Alexander, J. G. Kenna, J. Caldwell, and C. P. Day. 2004. Hepatic adducts, circulating antibodies, and cytokine polymorphisms in patients with diclofenac hepatotoxicity. Hepatology 39:1430-1440.
19. Li, J., X. Zhu, F. Liu, P. Cai, C. Sanders, W. M. Lee, and J. Uetrecht. 2010. Cytokine and autoantibody patterns in acute liver failure. J Immunotoxicol 7:157-164.
20. Feng, D., Y. Wang, Y. Xu, Q. Luo, B. Lan, and L. Xu. 2009. Interleukin 10 deficiency exacerbates halothane induced liver injury by increasing interleukin 8 expression and neutrophil infiltration. Biochem Pharmacol 77:277-284.
21. Kobayashi, M., S. Higuchi, K. Mizuno, K. Tsuneyama, T. Fukami, M. Nakajima, and T. Yokoi. 2010. Interleukin-17 is involved in alpha-naphthylisothiocyanate-induced liver injury in mice. Toxicology 275:50-57.
22. Higuchi, S., M. Kobayashi, Y. Yoshikawa, K. Tsuneyama, T. Fukami, M. Nakajima, and T. Yokoi. 2011. IL-4 mediates dicloxacillin-induced liver injury in mice. Toxicol Lett 200:139-145.

23. Kobayashi, E., M. Kobayashi, K. Tsuneyama, T. Fukami, M. Nakajima, and T. Yokoi. 2009. Halothane-induced liver injury is mediated by interleukin-17 in mice. Toxicol Sci 111:302-310.
24. Higuchi, S., M. Kobayashi, A. Yano, K. Tsuneyama, T. Fukami, M. Nakajima, and T. Yokoi. 2011. Involvement of Th2 cytokines in the mouse model of flutamide-induced acute liver injury. J Appl Toxicol.
25. Fontana, R. J., P. B. Watkins, H. L. Bonkovsky, N. Chalasani, T. Davern, J. Serrano, and J. Rochon. 2009. Drug-Induced Liver Injury Network (DILIN) prospective study: rationale, design and conduct. Drug Saf 32:55-68.
26. Rockey, D. C., L. B. Seeff, J. Rochon, J. Freston, N. Chalasani, M. Bonacini, R. J. Fontana, and P. H. Hayashi. 2010. Causality assessment in drug-induced liver injury using a structured expert opinion process: comparison to the Roussel-Uclaf causality assessment method. Hepatology 51:2117-2126.
27. Bell, L. N., R. Vuppalanchi, P. B. Watkins, H. L. Bonkovsky, J. Serrano, R. J. Fontana, M. Wang, J. Rochon, and N. Chalasani. 2012. Serum proteomic profiling in patients with drug-induced liver injury. Aliment Pharmacol Ther 35:600-612.
28. Steuerwald, N., J. Parsons, H. J. Norton, D. Saha, L. P. Chalasani, L. N. Bell, R. J. Fontana, P. B. Watkins, J. Serrano, and H. L. Bonkovsky. 2011. Chemokine/cytokine profiles in patients with acute DILI: results from the US Drug-Induced Liver Injury Network. Hepatology 54:Abstract 359.
29. Egwuagu, C. E. 2009. STATS in CD4+T helper cell differentiation and inflammatory diseases. Cytokine 47:149-156.
30. Jutel, M., and C. A. Akdis. 2011. T-cell subset regulation in atopy. Curr Allergy Asthma Rep 11:139-145.
31. Maeda, S., L. C. Hsu, H. Liu, L. A. Bankston, M. Iimura, M. F. Kagnoff, L. Eckmann, and M. Karin. 2005. Nod2 mutation in Crohn's disease potentiates NF-kappaB activity and IL-1beta processing. Science 307:734-738.
32. Mandal, P., M. T. Pritchard, and L. E. Nagy. 2010. Anti-inflammatory pathways and alcoholic liver disease: role of an adiponectin/interleukin-10/heme oxygenase-1 pathway. World J Gastroenterol 16:1330-1336.
33. Mumm, J. B., and M. Oft. 2010. Subversion and coercion: the art of redirecting tumor immune surveillance. Curr Top Microbiol Immunol 344:25-39.
34. Peduzzi, P., J. Concato, E. Kemper, T. R. Holford, and A. R. Feinstein. 1996. A simulation study of the number of events per variable in logistic regression analysis. J Clin Epidemiol 49:1373-1379.
35. Ciesielski, C. J., E. Andreakos, B. M. Foxwell, and M. Feldmann. 2002. TNFalpha-induced macrophage chemokine secretion is more dependent on NF-kappaB expression than lipopolysaccharides-induced macrophage chemokine secretion. Eur J Immunol 32:2037-2045.
36. Jaruga, B., F. Hong, W. H. Kim, R. Sun, S. Fan, and B. Gao. 2004. Chronic alcohol consumption accelerates liver injury in T cell-mediated hepatitis: alcohol disregulation of NF-kappaB and STATS signaling pathways. Am J Physiol Gastrointest Liver Physiol 287:G471-479.
37. Taima, K., T. Imaizumi, K. Yamashita, A. Ishikawa, T. Fujita, H. Yoshida, S. Takanashi, K. Okumura, and K. Satoh. 2006. Expression of IP-10/CXCL10 is upregulated by double-stranded RNA in BEAS-2B bronchial epithelial cells. Respiration 73:360-364.
38. Wiesner, R., E. Edwards, R. Freeman, A. Harper, R. Kim, P. Kamath, W. Kremers, J. Lake, T. Howard, R. M. Merion, R. A. Wolfe, and R. Krom. 2003. Model for end-stage liver disease (MELD) and allocation of donor livers. Gastroenterology 124:91-96.
39. Callan, H. E., R. E. Jenkins, J. L. Maggs, S. N. Lavergne, S. E. Clarke, D. J. Naisbitt, and B. K. Park. 2009. Multiple adduction reactions of nitroso sulfamethoxazole with cysteinyl residues of peptides and proteins: implications for hapten formation. Chem Res Toxicol 22:937-948.
40. Meng, X., R. E. Jenkins, N. G. Berry, J. L. Maggs, J. Farrell, C. S. Lane, A. V. Stachulski, N. S. French, D. J. Naisbitt, M. Pirmohamed, and B. K. Park. 2011. Direct evidence for the formation of diastereoisomeric benzylpenicilloyl haptens from benzylpenicillin and benzylpenicillenic acid in patients. J Pharmacol Exp Ther 338:841-849.
41. Whitaker, P., X. Meng, S. N. Lavergne, S. El-Ghaiesh, M. Monshi, C. Earnshaw, D. Peckham, J. Gooi, S. Conway, M. Pirmohamed, R. E. Jenkins, D. J. Naisbitt, and B. K. Park. 2011. Mass spectrometric characterization of circulating and functional antigens derived from piperacillin in patients with cystic fibrosis J Immunol 187:200-211.
42. Bonkovsky, H. L., and J. Brisbane. 1976. Colitis and hepatitis caused by methyldopa. JAMA 236:1602-1603.
43. Tujios, S., and R. J. Fontana. 2011. Mechanisms of drug-induced liver injury: from bedside to bench. Nat Rev Gastroenterol Hepatol 8:202-211.
Steuerwald et al Serum immune analytes in DILI Sep. 14, 2012
44. Uetrecht, J. 2009. Immunoallergic drug-induced liver injury in humans. Semin Liver Dis 29:383-392.
45. Nakashima, H., M. Akahoshi, and K. Masutani. 2006. Th1/Th2 balance of SLE patients with lupus nephritis. Rinsho Byori 54:706-713.
46. Cacoub, P., P. Musette, V. Descamps, O. Meyer, C. Speirs, L. Finzi, and J. C. Roujeau. 2011. The DRESS syndrome: a literature review. Am J Med 124:588-597.
47. Chalasani, N., R. Vuppalanchi, V. J. Navarro, R. J. Fontana, H. L. Bonkovsky, H. Barnhart, D. Kleiner, and J. H. Hoofnagle. 2012. Acute liver injury due to flavocoxid (Limbrel®), a medical food for osteoarthritis: a case series. Ann Intern Med In press.
48. Orman, E. S., H. S. Conjeevaram, R. Vuppalanchi, J. W. Freston, J. Rochon, D. E. Kleiner, and P. H. Hayashi. 2011. Clinical and histopathologic features of fluoroquinolone-induced liver injury. Clin Gastroenterol Hepatol 9:517-523 e513.
49. Vuppalanchi, R., P. H. Hayashi, N. Chalasani, R. J. Fontana, H. Bonkovsky, R. Saxena, D. Kleiner, and J. H. Hoofnagle. 2010. Duloxetine hepatotoxicity: a case-series from the drug-induced liver injury network. Aliment Pharmacol Ther 32:1174-1183.
50. Hammerich, L., F. Heymann, and F. Tacke. 2011. Role of IL-17 and Th17 cells in liver diseases. Clin Dev Immunol 2011:345803.
51. Aranami, T., and T. Yamamura. 2008. Th17 Cells and autoimmune encephalomyelitis (EAE/MS). Allergol Int 57:115-120.
52. Seiderer, J., I. Elben, J. Diegelmann, J. Glas, J. Stallhofer, C. Tillack, S. Pfennig, M. Jurgens, S. Schmechel, A. Konrad, B. Goke, T. Ochsenkuhn, B. Muller-Myhsok, P. Lohse, and S. Brand. 2008. Role of the novel Th17 cytokine IL-17F in inflammatory bowel disease (IBD): upregulated colonic IL-17F expression in active Crohn's disease and analysis of the IL17F p.His161Arg polymorphism in IBD. Inflamm Bowel Dis 14:437-445.

53. Hickman-Brecks, C. L., J. L. Racz, D. M. Meyer, T. P. LaBranche, and P. M. Allen. 2010. Th17 cells can provide B cell help in autoantibody induced arthritis. J Autoimmun 36:65-75.

That which is claimed:

1. A method of characterizing liver damage in a human subject, the method comprising:
   a. directly or indirectly obtaining a concentration value for serum albumin in a blood sample from the human subject;
   b. directly or indirectly obtaining a concentration value for one or more immune analytes selected from the group consisting of: TNFα; IL-12; IL-17; IL-4; IL-5; IL-13; IL-9; MIP-1β; RANTES; FGF b; and PDGF-bb in the blood sample from the human subject;
   c. determining if the serum albumin concentration value from step (a) is (i) less than or equal to 2.8 g/dL or (ii) greater than 2.8 g/dL;
   d. comparing the one or more immune analyte concentrations from step (b) with corresponding median immune analyte concentrations from healthy human subjects to determine if any of the one or more immune analyte concentrations from step (b) is less than the corresponding median immune analyte concentrations from healthy human subjects; and
   e. identifying the human subject as having
      i. life-threatening liver damage if the serum albumin concentration value from step (a) is less than or equal to 2.8 g/dL and each of the one or more immune analyte concentrations from step (b) is less than the corresponding median immune analyte concentrations from healthy human subjects; or
      ii. non-life-threatening liver damage if the serum albumin concentration value from step (a) is greater than 2.8 g/dL, and/or the immune analyte concentrations from step (b) are not all less than the corresponding median immune analyte concentrations from healthy human subjects.

2. The method of claim 1, further comprising one or more of the following:
   prescribing medical care appropriate for the human subject's identification status; and
   performing a liver transplant for the human subject if the human subject is identified as having life-threatening liver damage.

3. The method of claim 1, wherein the blood sample is a serum sample.

4. The method of claim 1, wherein step (b) comprises directly or indirectly obtaining concentration values for at least three immune analytes selected from the group consisting of TNFα, IL-12, IL-17, IL-4, IL-5, IL-13, IL-9, MIP-1β, RANTES, FGF b, PDGF-bb, and IL-6.

5. The method of claim 4, wherein step (b) comprises directly or indirectly obtaining concentration values for four immune analytes selected from the group consisting of TNFα, IL-12, IL-17, IL-4, IL-5, IL-13, IL-9, MIP-1β, RANTES, FGF b, PDGF-bb, and IL-6.

6. The method of claim 1, wherein step (b) comprises obtaining a concentration value for an immune analyte selected from the group consisting of IL-17, RANTES, and PDGF bb.

7. The method of claim 1, wherein step (b) comprises obtaining a concentration value for an immune analyte selected from the group consisting of IL-4, IL-13, IL-9, and FGF b.

8. The method of claim 1, wherein step (b) further comprises obtaining a concentration value for IL-6 in the blood sample from the human subject, wherein an IL-6 concentration value greater than the corresponding median immune analyte concentrations from healthy human subjects is consistent with identifying the human subject as having acute or sub-acute liver damage.

9. A method of assessing liver damage in a human subject, the method comprising:
   a. directly or indirectly obtaining a concentration value for serum albumin in a blood sample from the human subject;
   b. directly or indirectly obtaining concentration values for one or more immune analytes selected from the group consisting of: TNFα; IL-12; IL-17; IL-4; IL-5; IL-13; IL-9; MIP-1β; RANTES; FGF b; and PDGF-bb in the blood sample from the human subject;
   c. determining if the serum albumin concentration value from step (a) is (i) less than or equal to 2.8 g/dL or (ii) greater than 2.8 g/dL;
   d. comparing the one or more immune analyte concentrations from step (b) with corresponding median immune analyte concentrations from healthy human subjects to determine if any of the one or more immune analyte concentrations from step (b) is less than the corresponding median immune analyte concentrations from healthy human subjects; and
   e. identifying the human subject as having
      i. life-threatening liver damage if the serum albumin concentration value from step (a) is less than or equal to 2.8 g/dL and each of the one or more immune analyte concentrations from step (b) is less than the corresponding median immune analyte concentrations from healthy human subjects;
      ii. non-life-threatening liver damage if the serum albumin concentration from step (a) is greater than 2.8 g/dL, the immune analyte concentrations from step (b) are not all less than the corresponding median immune analyte concentrations from healthy human subjects, or both; or
      iii. normal liver function if the serum albumin concentration value from step (a) is greater than 2.8 g/dL and all of the one or more immune analyte concentrations from step (b) are greater than or equal to the corresponding median immune analyte concentrations from healthy human subjects.

10. The method of claim 9, wherein the blood sample is a serum sample.

11. The method of claim 9, wherein step (b) comprises directly or indirectly obtaining concentration values for at least three immune analytes selected from the group consisting of TNFα, IL-12, IL-17, IL-4, IL-5, IL-13, IL-9, MIP-1β, RANTES, FGF b, PDGF-bb, and IL-6.

12. The method of claim 9, wherein step (b) comprises directly or indirectly obtaining concentration values for four immune analytes selected from the group consisting of TNFα, IL-12, IL-17, IL-4, IL-5, IL-13, IL-9, MIP-1β, RANTES, FGF b, PDGF-bb, and IL-6.

13. The method of claim 9, wherein step (b) comprises directly or indirectly obtaining concentration values for IL-17, RANTES, PDGF-bb, and IL-9.

* * * * *